(12) United States Patent
Kassab et al.

(10) Patent No.: US 8,682,411 B2
(45) Date of Patent: Mar. 25, 2014

(54) DEVICES, SYSTEMS AND METHODS FOR EPICARDIAL CARDIAC MONITORING SYSTEM

(75) Inventors: Ghassan S. Kassab, Zionsville, IN (US); Jose Navia, Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 1033 days.

(21) Appl. No.: 12/522,279

(22) PCT Filed: Jan. 22, 2008

(86) PCT No.: PCT/US2008/000796
§ 371 (c)(1),
(2), (4) Date: Nov. 9, 2009

(87) PCT Pub. No.: WO2008/091584
PCT Pub. Date: Jul. 31, 2008

(65) Prior Publication Data
US 2010/0063375 A1    Mar. 11, 2010

Related U.S. Application Data

(60) Provisional application No. 60/881,471, filed on Jan. 22, 2007.

(30) Foreign Application Priority Data

Jun. 29, 2007   (WO) ................ PCT/US2007/015207

(51) Int. Cl.
*A61B 5/04*   (2006.01)
(52) U.S. Cl.
USPC ............ 600/375; 600/372; 600/373; 600/374
(58) Field of Classification Search
None
See application file for complete search history.

(56) References Cited

U.S. PATENT DOCUMENTS

| | | | |
|---|---|---|---|
| 4,646,747 A * | 3/1987 | Lundback | ...... 600/387 |
| 5,313,953 A | 5/1994 | Yomtov et al. | |
| 5,339,823 A | 8/1994 | Reinhold, Jr. | |
| 6,073,046 A | 6/2000 | Patel et al. | |
| 6,110,100 A | 8/2000 | Talpade | |
| 6,155,267 A * | 12/2000 | Nelson | .......... 128/899 |
| 2002/0151889 A1 | 10/2002 | Swanson et al. | |
| 2003/0171796 A1 | 9/2003 | Hine et al. | |
| 2005/0119648 A1* | 6/2005 | Swanson | .......... 606/41 |
| 2005/0234360 A1 | 10/2005 | Richardson | |
| 2005/0273015 A1* | 12/2005 | Bauer et al. | .......... 600/528 |
| 2006/0122522 A1 | 6/2006 | Chavan et al. | |
| 2006/0161238 A1 | 7/2006 | Hall | |
| 2006/0293740 A1 | 12/2006 | Heil, Jr. et al. | |

OTHER PUBLICATIONS

PCT/US2008/000796, International Searching Authority, PCT Search Report and Written Opinion, dated Sep. 10, 2008.

\* cited by examiner

*Primary Examiner* — Michael Kahelin
*Assistant Examiner* — Mitchell Alter
(74) *Attorney, Agent, or Firm* — Reichel IP LLP; Mark C. Reichel; Kevin R. Erdman

(57) ABSTRACT

Devices, systems, and methods for remotely monitoring physiologic cardiovascular data are disclosed. At least some of the embodiments disclosed herein provide access to the external surface of the heart through the pericardial space for the delivery of the sensor to the epicardial surface of the heart. In addition, various disclosed embodiments provide for a memory device capable of receiving the physiologic cardiovascular data collected by the sensors and transmitting such data wirelessly to a remote location.

58 Claims, 13 Drawing Sheets

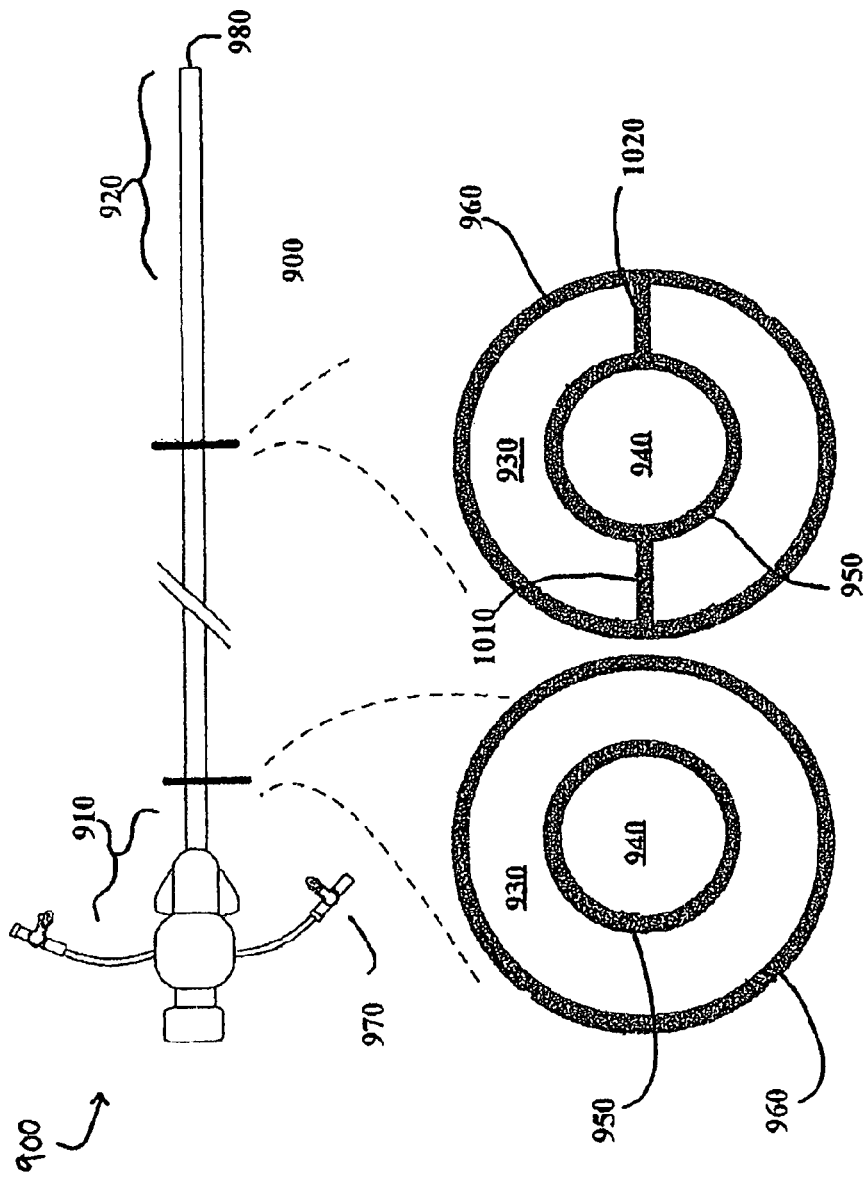

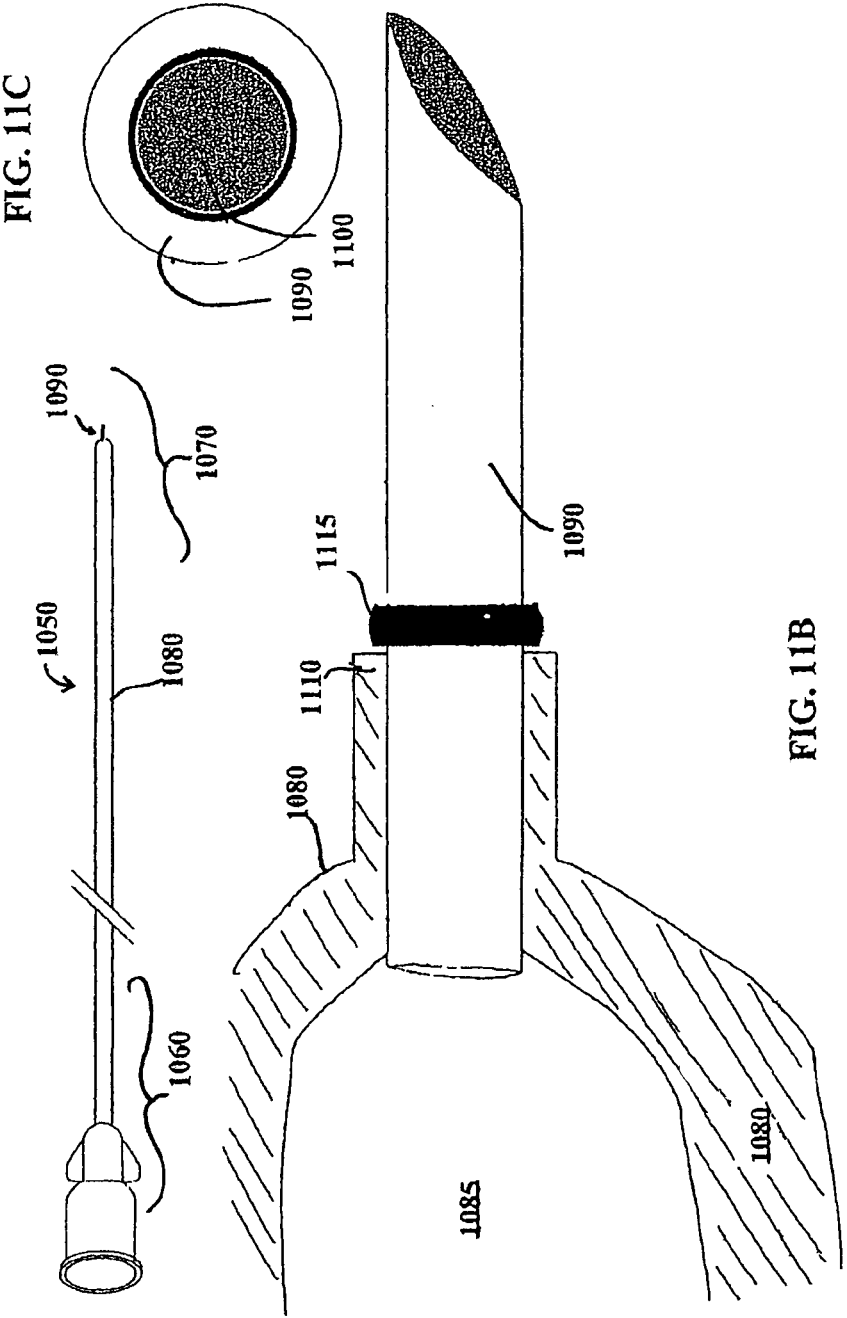

DEVICES, SYSTEMS AND METHODS FOR EPICARDIAL CARDIAC MONITORING SYSTEM

PRIORITY

The present application is related to, and claims the priority benefit of, International Patent Application Serial No. PCT/US2008/000796, filed Jan. 22, 2008, which: (1) is related to, and claims the priority benefit of, U.S. Provisional Patent Application Ser. No. 60/881,471, filed Jan. 22, 2007, and (2) is related to, and claims the priority benefit of, International Patent Application Serial No. PCT/US2007/015207, filed Jun. 29, 2007, which is related to, and claims the priority benefit of, U.S. Provisional Patent Application Ser. No. 60/817,421, filed Jun. 30, 2006. The contents of each of these applications are hereby incorporated by reference in their entirety into this disclosure.

BACKGROUND

A healthy cardiac rhythm not only consists of a heart that beats at the proper pace, but the muscular contractions of the four chambers of the heart must also be properly mediated such that they can contract in a coordinated fashion. The heart has specialized conduction pathways in both the atria and the ventricles that enable the rapid conduction of excitation (i.e. depolarization) throughout the myocardium. Normally, the sinoatrial node ("SA node") initiates each heart-beat cycle by depolarizing so as to generate an action potential. This action potential propagates relatively quickly through the atria, which react by contracting, and then relatively slowly through the atrio-ventricular node ("AV node"). From the AV node, activation propagates rapidly through the His-Purkinje system to the ventricles, which also react by contracting. This natural propagation synchronizes the contractions of the muscle fibers of each chamber and synchronizes the contraction of each atrium or ventricle with the contralateral atrium or ventricle.

The rate at which the SA node depolarizes determines the rate at which the atria and ventricles contract and thus controls the heart rate. The pace at which the SA node depolarizes is regulated by the autonomic nervous system which can alter the heart rate so that the heart, for instance, beats at a faster rate during exercise and beats at a slower rate during rest. The above-described cycle of events holds true for a healthy heart and is termed normal sinus rhythm.

The heart, however, may have a disorder or disease that results in abnormal activation preempting sinus rhythm, and resulting in an irregular heartbeat, i.e. an arrhythmia. Individuals with cardiac ailments, and especially those at risk of sudden cardiac death ("SCD"), may suffer from an irregular pace and/or uncoordinated mechanical activity wherein the myocardial depolarization and contraction of the chambers do not occur simultaneously. Without the synchronization afforded by the normally functioning specialized conduction pathways or the proper pacing by the SA node, the heart's pumping efficiency is greatly diminished and can thus compromise a patient's cardiac output. Several different factors may lead to the development of an arrhythmia, including atherosclerosis, thrombosis, defects in electrogenesis and nerve impulse propagation, influences of the sympathetic and parasympathetic systems, ischemia (inadequate oxygen supply to the cells due to lack of blood flow), and/or poor vascular control.

Despite advances in techniques of resuscitation, cardiac arrest and related cardiac disorders such as those mentioned above are associated with significant rates of morbidity and mortality. Due to the increasing incidence of SCD, chronic heart failure, and other life threatening cardiac ailments, cardiac dysfunction remains a major public health problem, especially in developed countries. For example, it is estimated that between cases of 250,000 and 300,000 occur per year in the United States.

As patients age and/or exhibit habits that increase their risk of heart disease, certain heart ailments appear suddenly, while others develop slowly over a period of time. In the cases where it seems as if the heart ailment has suddenly appeared (e.g., SCD), it is often the case that cardiac episodes have previously occurred, yet, due to the absence of noticeable pain, have gone undetected. For example, an estimated half of the 3-4 million Americans that suffer from heart attacks per year, suffer from "silent" infarctions that are not felt by the patients. In any event, individuals that experience traumatic cardiac events tend to have suffered from a series of preceding cardiac difficulties that occurred over an extended period of time.

A certain degree of damage results with each detrimental episode that the heart undergoes. This damage may manifest itself through altering the cardiac structure, altering the contractile function of the heart, and/or damaging the heart's electrical system. When a patient exhibits damage to the electrical system of the heart in particular, severe issues may arise without the patient's detection. For example, in about 30% of chronic heart failure patients, the disease process compromises the myocardium's ability to contract, which thereby alters the conduction pathways through the heart. This conduction disturbance can cause a delay in the beginning of right or left ventricular systole and thereby induce asynchronous atrial and ventricular activation. Atrial fibrillation and malignant ventricular arrhythmia are two examples of such arrhythmias that may result from cardiac disease, both of which often prove deadly. Atrial fibrillation in particular is one of the most commonly encountered arrhythmias, and it is correlated with increased mortality and morbidity due to thromboembolic complications, especially with respect to undetected asymptomatic atrial fibrillation. Furthermore, alterations in ventricular contractility and ventricular volume are frequently followed by cardiac decompensation, leading to severe symptoms and the necessity for immediate hospitalization.

While arrhythmias are detectable on an electrocardiogram ("ECG") and are often treatable, as previously noted, the patient may be wholly unaware of the occurrence. If left untreated over time, in some patients an arrhythmia can lead to clinical instability and an increased risk of death. Accordingly, it is common for patients with chronic heart failure or other similar cardiac diseases to exhibit minimal or no symptoms, followed by—what appears at least to the patient to be—a sudden, drastic cardiac event that either requires immediate hospitalization or results in death.

In patients at increased risk for cardiac difficulties, such as those patients with chronic heart failure, continuous monitoring of cardiovascular data is critical. For example, in patients with chronic heart failure, right ventricle hemodynamic monitoring, left ventricle wall motion, and ECGs each provide important clinical information with a favorable impact on outcome. However, conventional monitoring devices are typically bulky and not conducive to daily activities. As previously mentioned, one common monitoring system for monitoring a patient's cardiovascular data is an ECG. An ECG records electrical signals from the heart via a series of electrodes attached to the patient's chest. Typically ECG equipment is large and cumbersome, and is not suitable for a patient to use after release from the hospital. Further, ECG results are not easy to decipher and are typically reviewed by a healthcare practitioner who is qualified to translate the results.

Another type of monitoring system is a Holter monitor, or an ambulatory electrocardiography device. The Holter monitor comprises a portable memory device for recording cardiovascular data collected through multiple ECG leads attached to the patient's chest. The memory device can be worn on a belt or in a case on a strap worn across the patient's chest. Due to the size of the leads and the Holter monitor's required placement, it is recommended that individuals wearing the Holter device wear layers or bulky clothes to disclose the ECG leads attached to their chest. In addition, because of the requisite placement of the leads, individuals who desire to wear the Holter device discretely must wear shirts with a high neck so as to disclose the entirety of the electrodes.

Typically, the Holter monitor is applied to the patient for only 24 hours. Accordingly, the patient must report back to the physician's office periodically to return the equipment and deliver the memory device. Thereafter, the information collected must be reviewed, and the signals inspected to determine if any cardiovascular abnormality occurred within the previous 24 hours.

Accordingly, monitoring devices capable of continuously monitoring the cardiovascular data of a patient are cumbersome due to the nature of conventional monitoring equipment. Due to the growing number of patients exhibiting cardiac disorders, there is a need for a technique and system that allows for early detection and long term, unburdensome monitoring of heart related disorders. Furthermore, such novel techniques and equipment should be easy to understand and implement, universally adoptable, and have competitive advantages over conventional heart monitoring devices, such as ECGs and Holter monitors.

SUMMARY

Various embodiments disclosed herein relate to systems and devices of a portable monitoring system that is capable of providing continuous, remote monitoring of a heart. Further, various embodiments disclosed relate to methods for delivering sensors to the epicardial surface of a heart such that continuous, remote observation of the heart function can be achieved. For example, using certain embodiments, a sensor may be delivered to a specifically targeted area of the external wall of the heart (i.e. "targeted tissue"). Certain other embodiments provide for access to the tissue on the external surface of the heart by delivering a device to the pericardial space using a non-surgical, percutaneous route that is both rapid and safe.

At least some of the embodiments disclosed herein include a system for monitoring the physiologic cardiovascular data of a heart from the epicardial surface. Such system comprises a sensory lead, a connecting wire and a memory device. The sensory lead is coupled with the memory device through the connecting wire and comprises a connection assembly and at least one sensor for collecting physiologic data from a targeted tissue. In certain embodiments, the connection assembly may be configured to traverse and/or seal an opening in the wall of the heart. In one embodiment, the system also includes a memory device positioned subcutaneously on the patient that is capable of transmitting the data received from the sensors to a remote location, such as a computer or processor. For example and without limitation, the memory device may send the data wirelessly, through telemetry or the interne. Further, the memory device is programmable such that it can process the data received from the sensory lead.

In various embodiments, the sensors of the sensory lead have an attachment mechanism. The attachment mechanisms function to facilitate the secure and stable attachment of the sensors to the surface of the heart. The attachment mechanism may comprise a pinching mechanism, an adhesive mechanism, a suction mechanism, or any combination thereof. In one embodiment, the attachment mechanism comprises a scaffold assembly having a body, a first delivery channel and a plurality of openings. The sensor is coupled with the body of the scaffold assembly. In this embodiment, the attachment mechanism further comprises a delivery catheter having a proximal end, a distal end, and first and second lumens extended between the proximal end and the distal end. Further, the first lumen comprises a second delivery channel that is in fluid communication with the first delivery channel of the scaffold assembly. The second lumen comprises a wire channel for encasing the connecting wire of the sensor. This attachment mechanism facilitates the attachment of the sensor to the epicardial surface of a heart by delivering an adhesive through the delivery channel of the delivery catheter, which is advanced to the delivery channel of the scaffold assembly and released around the sensor through the plurality of openings in the scaffold assembly. In this manner, an adhesive is employed to facilitate a secure connection between the epicardial surface of a heart and the sensor.

Also disclosed are other embodiments of an attachment mechanism. In this embodiment, the attachment mechanism comprises a single-chambered capsule comprising a flexible exterior wall having an open end, a closed end and an interior. A disk is disposed within the closed end of the capsule and is releasably coupled with a sensor such that the sensor extends into the interior of the capsule. A vacuum catheter is coupled with the exterior wall of the capsule and is in communication with the interior thereof. When this embodiment of the attachment mechanism is applied to the surface of the heart, a vacuum is created within the interior of the capsule, which shifts the capsule from an upright position to a collapsed position. In so doing, the sensor is inserted into the wall of the heart. Thereafter, the sensor is released from the disk and the remainder of the attachment mechanism is withdrawn from the body, leaving the sensor securely in place.

Certain embodiments of the attachment mechanism further comprise a double-chambered capsule comprising an exterior wall, an open end, a closed end, and an interior space. A flexible membrane is disposed across the interior space of the capsule, thereby defining an upper chamber and a lower chamber. A vacuum catheter is coupled with the exterior wall of the capsule and in communication with the lower chamber. A delivery catheter is coupled with the exterior wall of the capsule and in communication with the upper chamber. The disk is coupled with the flexible membrane, and at least one sensor is releasably coupled with the disk such that the sensor extends into the lower chamber. The open end of the capsule is configured to removably attach to a targeted tissue such that the application of suction to the vacuum catheter is capable of forming a reversible seal with the targeted tissue, and the flexible membrane is capable of shifting from a first upright position to a second collapsed position when a gas is introduced into the upper chamber through the delivery catheter and suction is applied through the catheter.

At least one embodiment of the disclosed monitoring systems may be delivered to the patient's heart through operation of catheterization and a percutaneous procedure. A system is provided comprising an engagement catheter having a proximal end, a distal end and a first and second lumen extending between the proximal and distal ends; a first delivery catheter comprising a proximal end, a distal end, and a hollow tube extending between the proximal end and the distal end. Further the first delivery catheter is configured for insertion into the second lumen of the engagement catheter. A needle is also provided at the distal end of the first delivery catheter and a vacuum port is located at the proximal end of the engagement catheter. A second delivery catheter is also provided and is comprised similarly to the first delivery catheter, except that the second delivery catheter does not comprise a needle. Embodiments of this system may be used to deliver embodiments of the monitoring system to a heart.

Certain other embodiments include the steps of extending into a blood vessel an elongated hollow tube having a proximal end, a distal end, and at least one lumen, such that the distal end of the tube is in contact with the interior wall of the heart; aspirating the targeted tissue on the interior wall of the heart such that the wall of the heart is retracted away from a pericardial sac surrounding the heart to enlarge a pericardial space between the pericardial sac and the wall of the heart; delivering a first catheter comprising a needle through the interior of the elongated tube and puncturing the interior wall of the heart with the needle; accessing the pericardial space through the puncture; inserting a second catheter containing the monitoring system to be implanted and delivering components of the monitoring system into the pericardial space; and removing the elongated tube from the body. In at least some embodiments, when the needle is withdrawn after puncture, the distal end of a guide wire is inserted through the lumen of the catheter and into the pericardial space prior to inserting the second catheter into the pericardial space. Such embodiments may further include the steps of attaching the memory device of the monitoring system subcutaneously on the body.

BRIEF DESCRIPTION OF THE DRAWINGS

FIG. 10A shows at least one embodiment of an engagement catheter;

FIG. 10B shows a cross-sectional view of the proximal end of the engagement catheter of FIG. 10A;

FIG. 10C shows a cross-sectional view of the distal end of the engagement catheter of FIG. 10A;

FIG. 11A shows at least one embodiment of a delivery catheter;

FIG. 11B shows a close-up view of the needle shown in FIG. 11A; and

FIG. 11C shows a cross-sectional view of the needle shown in FIGS. 11A and 11B.

DETAILED DESCRIPTION

Figure 1A:
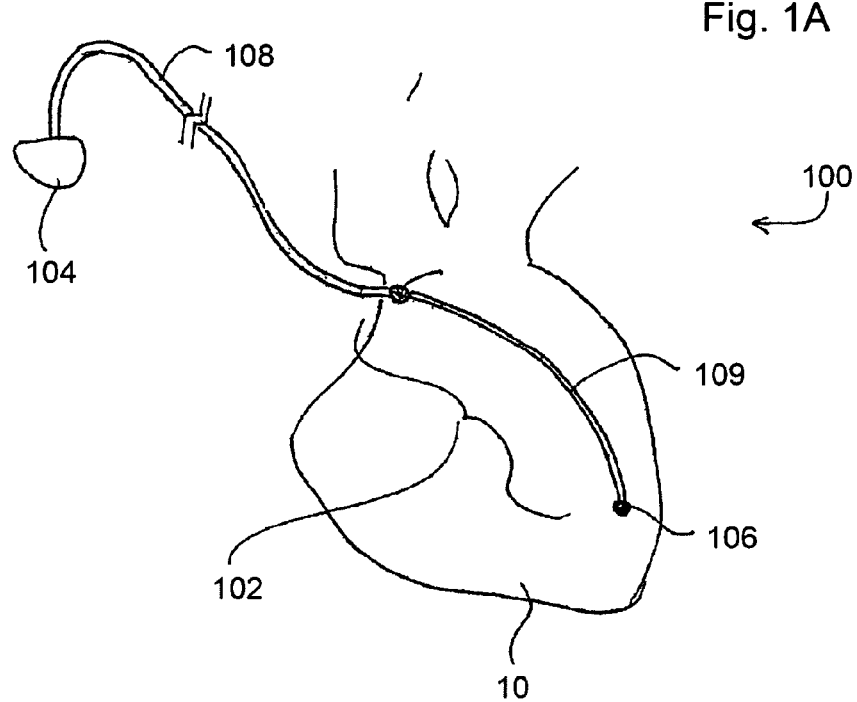
FIG. 1A shows a front view of at least one embodiment of an implantable monitoring device for attachment to on an epicardial surface.

Reference will now be made to the embodiments illustrated in the drawings and specific language will be used to describe the same. It will nevertheless be understood that no limitation of scope of the appended claims is intended by the description of these embodiments. For example, while at least one of the embodiments described herein is described with respect to the heart, such embodiments may also be applied to other organs of a body, including, without limitation, the lungs, stomach, and gastrointestinal tract.

The disclosed embodiments include devices, systems and methods useful for remotely monitoring a patient's physiologic data and overall health. Further, at least one embodiment of the devices, systems and methods disclosed provides for the noninvasive and stable application of sensors to the surface of a heart such that continuous physiologic monitoring may be achieved. By allowing for continuous observation of a patient's cardiovascular data over a long term basis, a physician can 1) monitor the long-term characteristics of cardiovascular parameters; 2) observe alterations in hemodynamic parameters that take place during significant clinical events; and 3) explore the utility of long term hemodynamic information in changing the treatment management and reduction in hospitalizations. Further, the embodiments disclosed herein do not require that the patient be confined in the hospital. As such, the patient can return to his or her daily routines all while enjoying a reduced level of stress and related anxiety with respect to his or her condition, as he or she may be comforted by the fact they are being continuously monitored.

FIG. 1A shows at least one embodiment of a monitoring system 100 for monitoring cardiovascular physiologic data.

The monitoring system 100 comprises a sensory lead 102, a memory device 104, and a first connecting wire 108. In this embodiment, the first connecting wire 108 is coupled with both the sensory lead 102 and the memory device 104 such that the sensory lead 102 and the memory device 104 can exchange data and electrical energy between one another. Briefly, in one embodiment, when the monitoring system 100 is positioned within the patient, the sensory lead 102 is inserted through catheterization and transcutaneous puncture into the pericardial space proximate to the surface of the heart 10. Further, the connecting wire 108 coupled with the connection assembly 105 of the sensory lead 102 extends from the interior of the heart 10 to the memory device 104 that is implanted subcutaneously.

In the at least one embodiment of the monitoring system 100 shown in FIG. 1A, the memory device 104 is any device capable of receiving, storing, and transmitting data. In at least one embodiment, the memory device 104 is configured to transmit data to a remote location using telemetry, the internet, or any other means of wireless transmission. Further, the memory device 104 may also be capable of performing programmed operations on data stored therein. For example, the memory device 104 may process and organize received data prior to transmitting such data to a remote location. In the at least one embodiment shown in FIG. 1A, the memory device 104 is inserted subcutaneously on the patient. For example, the memory device 104 may be positioned subcutaneously beneath the right or left clavicle of the patient. In this manner, the memory device 104 may be accessed in a manner minimally invasive to the patient.

As previously described, the memory device 104 is coupled with the sensory lead 102 through the first connecting wire 108. The first connecting wire 108 comprises a proximate end and a distal end and may be any conduit through which a data signal and/or electrical energy may be transferred from the sensory lead 102 to the memory device 104. The proximate end of the connecting wire 108 is coupled with the memory device 104. When the memory device 104 is inserted subcutaneously, the first connecting wire 108 extends through either the jugular or femoral vein and the superior or inferior vena cava, respectively, in a fashion similar to the insertion of a pacemaker unit (e.g., catheterization). Within the interior of the heart 10, the distal end of the first connecting wire 108 couples with the connection assembly 105 of the sensory lead 102.

Figure 1B:
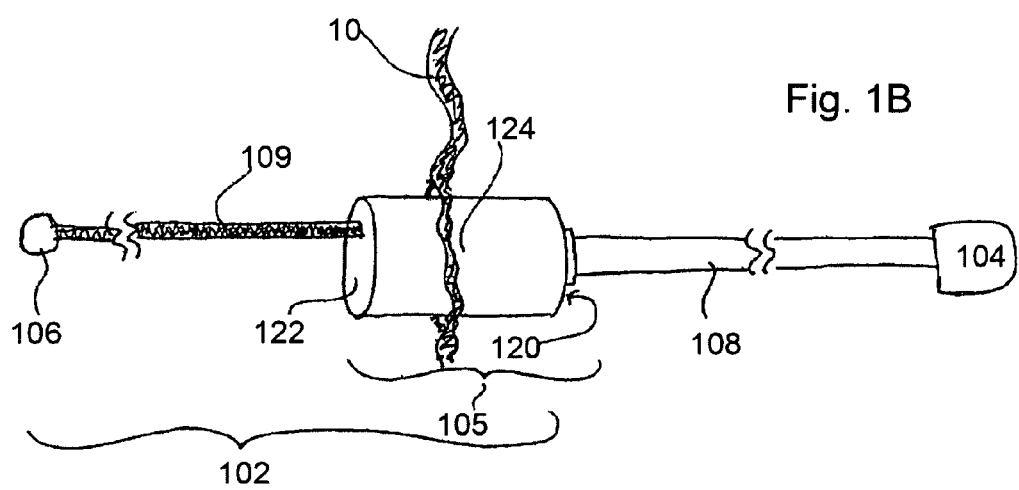
FIG. 1B shows a perspective view of one embodiment of a connection assembly of the monitoring device of FIG. 1A.

In FIG. 1B, details of the sensory lead 102 are shown. Generally, the sensory lead 102 comprises any device that is capable of collecting physiologic data from the epicardial surface of a heart 10. In one embodiment, the sensory lead 102 includes a connection assembly 105 and a sensor 106 coupled together by a second connecting wire 109. As the connection assembly 105 is also coupled with the memory device 104 through the first connecting wire 108, the connection assembly 105 of the sensory lead 102 enables the transfer of data and electrical energy between the sensor 106 and the memory device 104. The connection can be located over the epicardial surface or at the level of the atrial wall puncture (at the entrance of the epicardial sac). The size of the catheter can include a sealing system for example, a biodegradable adhesive material (fibrin glue, cianometacrilate, etc.). The plug may be made from any suitable material, including casein, polyurethane, silicone, and polytetrafluoroethylene.

The connection assembly 105 of the sensory lead 102 specifically comprises a first end 120, a second end 122, and a body 124. The first end 120 of the connection assembly 105 is coupled with the connecting wire 108 and the second end 122 of the connection assembly 105 is coupled with the second connecting wire 109. In the embodiments shown in FIGS. 1A and 1B, the body 124 of the connection assembly 105 is configured to traverse an opening in the wall of the heart 10. In one embodiment, the opening may be in the atrial wall. In another embodiment, the opening may be in the atrial appendage. In yet another embodiment, the body 124 of the connection assembly 105 is configured to substantially plug the opening through which it is applied, thereby preventing any leaks from within the heart 10 into the pericardial sac. In this embodiment, the connection assembly 105 may be comprised of any suitable material, including without limitation, casein, polyurethane, silicone, and/or polytetrafluoroethylene.

Although the connection assembly 105 has been described as traversing the wall of the heart 10 with respect to this embodiment, the connection assembly 105 of the sensory lead 102 may be positioned in any location within the body of the patient, provided that the placement of the connection assembly 105 allows for the connection assembly 105 to adequately function as a conduit between the memory device 104/first connecting wire 108 and the sensory lead 102. For example, in at least one embodiment, the connection assembly 105 is positioned on the epicardial surface of the heart 10. In this embodiment, after the connection assembly 105 is delivered to the surface of the heart 10 through an opening, a delivery catheter is used to seal the opening in the wall of the heart 10 (as described in more detail below).

As previously described, the sensor 106 is in communication with the connection assembly 105 through the second connecting wire 109. The sensor 106 is configured to attach to the epicardial surface of the heart 10 and is capable of obtaining physiologic cardiovascular data therefrom. For example, the sensor 106 may be employed to collect hemodynamic data, pressure data, data regarding depolarization and repolarization, or any other type of data that is collectable through a sensor. The sensor 106 may comprise microtransducers, piezo crystals, pressure sensors, or any other device capable of obtaining data from a tissue or organ when the sensor 106 is coupled therewith. In at least one embodiment, the sensor 106 receives power from the memory device 104 through the first connecting wire 108. As the memory device 104 may be positioned subcutaneously, the power supply for the sensor 106 may be easily and noninvasively recharged or replaced without accessing the epicardial surface.

In at least one embodiment, the sensor 106 further comprises a mechanism to facilitate the secure attachment of the sensor 106 to a target epicardial surface. In this embodiment, the attachment mechanism may comprise a pinching mechanism, an adhesive mechanism, a penetrating mechanism, or any other mechanism capable of facilitating the secure attachment of the sensor 106 to the target epicardial surface (described in more detail with respect to FIGS. 5-7B). Through the use of the attachment mechanism, the sensor 106 may be securely anchored in position on the target tissue. Accordingly, the use of the attachment mechanism in conjunction with the sensor 106 decreases the risk that the inherent movement of the functioning heart will detrimentally affect the quality or amount of data collected by the sensor 106.

Figure 2:
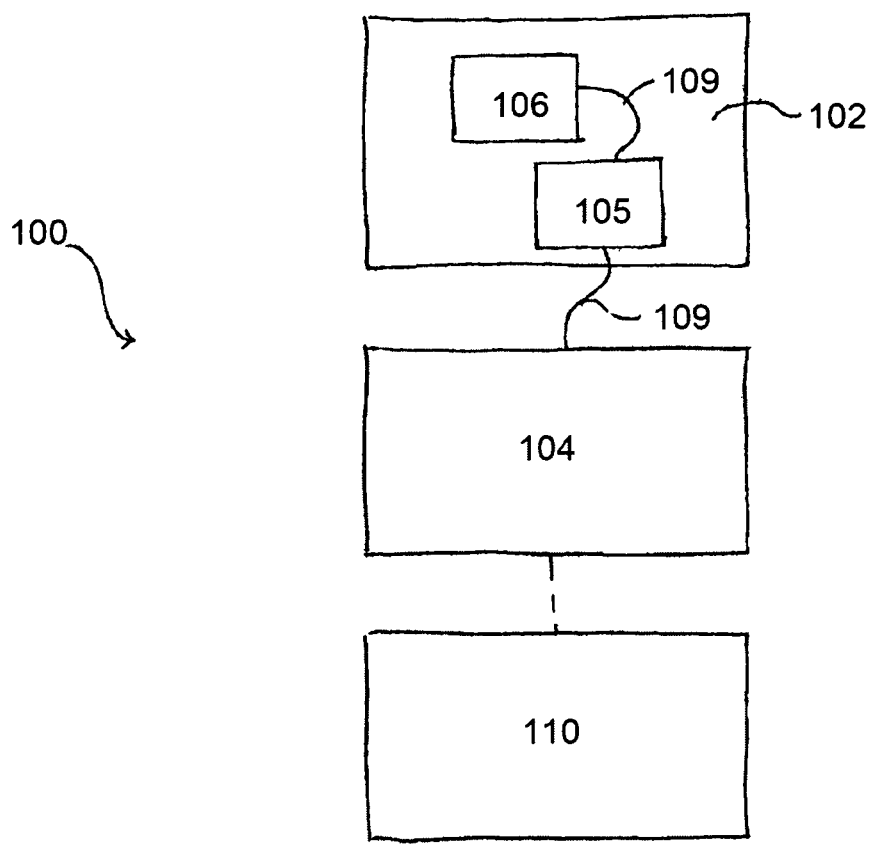
FIG. 2 shows a schematic view of at least one embodiment of an implantable monitoring device for attachment to an epicardial surface.

Now referring to FIG. 2, a schematic representation of at least one embodiment of the monitoring system 100 is shown. In this embodiment, the monitoring system 100 further comprises a remote processor 110. The remote processor 110 comprises any processing means known in the art, including without limitation, a server, remote computer, or remote handheld device, provided the processing means is capable of receiving data transmitted by the memory device 104. In one embodiment, the remote processor 110 further comprises a display device such that a user at a remote location can view the data collected by the sensor 106.

In operation, the monitoring system 100 functions to collect data from the surface of the heart 10 and to either store such collected data in the memory device 104 or transmit such information to a remote location, such as the remote processor 110. Specifically, the sensor 106 obtains information from the epicardial tissue to which the sensor 106 is attached. The collected data is transferred through the second connecting wire 109, the connection assembly 105, and the first connecting wire 108 to the memory device 104. The memory device 104 receives the collected data and either stores the collected data for a period of time, or immediately transmits the collected data to the remote processor 110 via a wireless connection. In one embodiment, the memory device 104 is programmed to transmit the collected data intermittently to the remote processor 110 at preset intervals. In an alternative embodiment, the memory device 104 is programmed to transmit the collected data to the remote processor 110 in a continuous stream.

When the data is received by the remote processor 110, a clinician can monitor the collected data from a remote location. In this manner, a patient may reside in the comfort of his or her own home, yet be continuously monitored for an impending or severe cardiovascular event. In addition, the data collected by the monitoring system 100 can provide guidance in selecting and/or modifying the medical therapy that the patient is receiving.

In at least one alternative embodiment, the memory device 104 may be programmed to process the collected data prior to transmitting the data to the remote processor 110. Accordingly, after the memory device 104 receives the collected data from the sensory lead 102, the memory device 104 performs preprogrammed operations on the collected data to reduce the need for processing the data at the remote processor 110. For example, and without limitation, the memory device 104 may be programmed to organize and interpret the data prior to transmission. In this at least one embodiment, the remote processor 110 need not be capable of performing processing functions and can merely be used to display the processed data. This may be particularly useful if a clinician wishes to receive the collected data on a device that does not necessarily support complex data processing programs, such as a handheld device.

Figure 3:
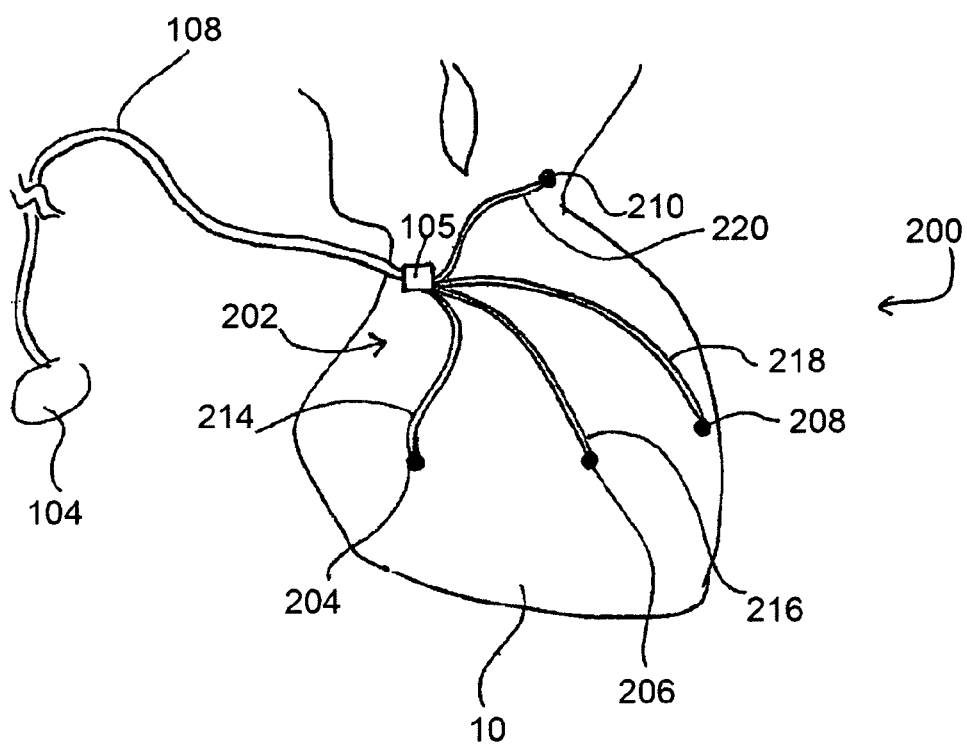
FIG. 3 shows a front view of at least one embodiment of an implantable monitoring device for attachment to on an epicardial surface.

Now referring to FIG. 3, an alternative embodiment of the monitoring system 100 is shown. A monitoring system 200 comprises components identical to those of monitoring system 100 of FIGS. 1A and 1B, except that the sensory lead 202 of the monitoring system 200 comprises multiple sensors: a first sensor 204, a second sensor 206, a third sensor 208, and a fourth sensor 210. In this embodiment, each of the four sensors 204, 206, 208, 210 is coupled with an independent connecting wire 214, 216, 218, 220, respectively. Further, each of the connecting wires 214, 216, 218, 220 is coupled with the connection assembly 105 such that the data collected from each of the sensors 204, 206, 208, 210 is transferred through the connection assembly 105, the first connecting wire 108, and to the subcutaneous memory device 104. Although the sensory lead 202 shown in FIG. 3 comprises four sensors 204, 206, 208, 210, the sensory lead 202 may include any number of sensors.

The sensors may be positioned at various locations on the epicardial surface of the heart 10 in order to obtain the desired data. FIG. 3 shows the sensors 204, 206, 208, 210 strategically positioned to collect specific data from different locations of the heart 10 in order to detect complications. For example, in FIG. 3 each of the sensors 204, 206, 208, 210 are positioned on the heart 10 to monitor the following data: the sensor 204 is positioned to collect electrogram data (e.g. heart rate, arterial fibrillation, and/or premature ventricular contraction data), the sensor 206 is positioned to monitor coronary flow-velocity, the sensor 208 is positioned to monitor left ventricular wall motion (i.e. to determine wall thickness, segmental shortening, etc.), and the sensor 210 is positioned to monitor the right ventricle hemodynamic outflow. Although these positions are referenced herein by way of example, the sensors 204, 206, 208, 210 may be positioned on any area of the epicardial surface of the heart 10.

Referring back to the sensors 106, 204, 206, 208, 210 of the above described monitoring systems 100, 200, several embodiments of the attachment mechanism of the sensor 106 are described. While the singular term "the sensor 106" is used herein in describing several embodiments, it will be recognized that any type or number of sensors may be employed.

As previously indicated, one embodiment of the sensor 106 may comprises a mechanism to facilitate the secure attachment of the sensor 106 to the target epicardial surface. Now referring to FIG. 4A, a bottom view of one embodiment of a sensor 106 having an attachment mechanism 415 is shown. The attachment mechanism 415 comprises an adhesive mechanism and functions to secure a sensor 106 to the epicardial surface of the heart 10 using an adhesive.

Figure 4A:
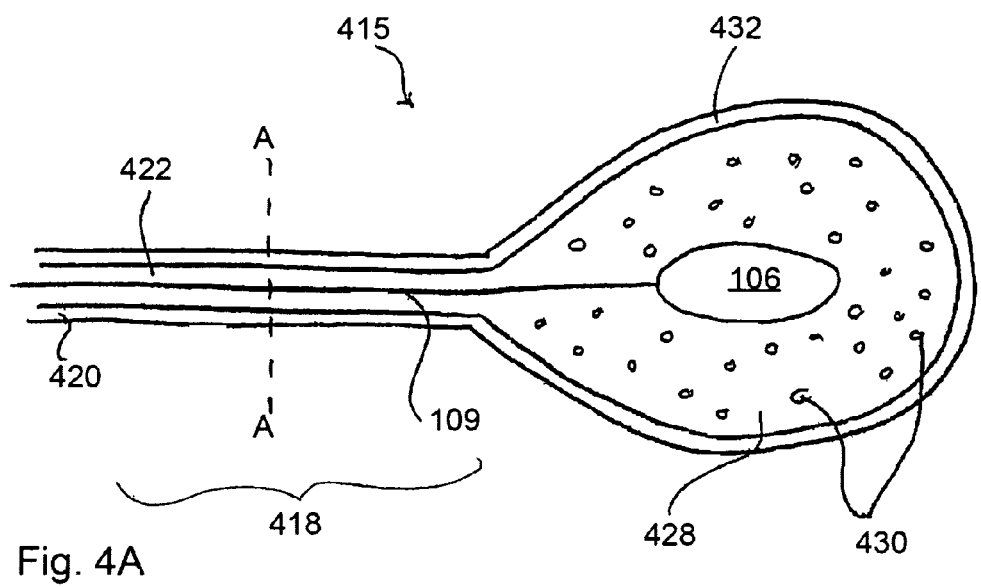
FIG. 4A shows a bottom view of at least one embodiment of a sensor of an implantable monitoring system having an attachment mechanism coupled therewith.

In this embodiment, the attachment mechanism 415 comprises a delivery catheter 418 coupled with a scaffold assembly 428. The scaffold assembly 428 comprises a body having a top portion and a bottom portion. Additionally, in one embodiment, the body of the scaffold assembly 428 further comprises a plurality of magnetic beads 430 or biologic glue embedded therein. The sensor 106 is embedded within the bottom portion of the scaffold assembly 428. The body of the scaffold assembly 428 can be configured in any shape or size, provided the scaffold system 428 surrounds the perimeter of the sensor 106. For example, and without limitation, the body of the scaffold assembly 428 shown in FIG. 4A is configured in a circular shape and the sensor 106 is disposed in the center of the bottom portion of the ferromagnetic scaffold assembly 428 such that at least a portion of the sensor 106 is exposed to contact the tissue (see FIG. 4C). Additionally, in the embodiment shown in FIG. 4A, the plurality of magnetic beads 430 or biologic glue surrounds the sensor 106.

In at least one embodiment, the scaffold assembly 428 further comprises a delivery channel 432 that extends around its periphery. The scaffold assembly 428 also has a number of openings that are in fluid communication with the delivery channel 432 and can be used to transmit fluid or a viscous material from the delivery channel 432 to a tissue in close proximity to the attachment mechanism 415.

Figure 4B:
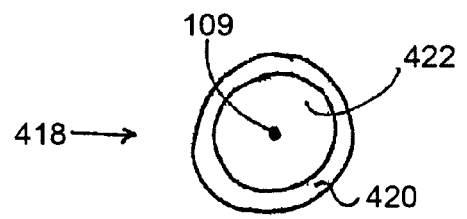
FIG. 4B shows a cross-sectional view of the delivery catheter of the attachment mechanism of FIG. 4A along line A-A.
Figure 4C:
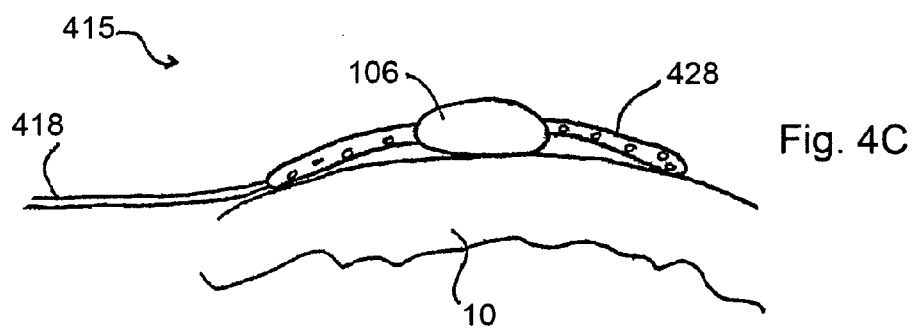
FIG. 4C shows a cross-sectional view of the attachment mechanism of FIG. 4A coupled with an epicardial surface of a heart.

In yet another embodiment, the scaffold assembly 428 exhibits a degree of flexibility and thus the attachment mechanism 415 can be moved between a first folded position (not shown) and a second open position (see FIGS. 4A and 4B). When the attachment mechanism 415 is in the first folded position, the attachment mechanism 415 is rolled up in such a fashion that the folded scaffold assembly 428 and the sensor 106 embedded therein can be easily advanced through a lumen or a catheter. However, when the attachment mechanism 415 is extended to the second open position, the ferromagnetic scaffold system 428 comprises a flat, open structure capable of affixing to a substantially flat or irregular surface. Further, when the scaffold assembly 428 is positioned in the second open position, at least a portion of the sensor 106 is exposed and capable of coupling with a targeted tissue.

Referring back to FIG. 4A, the attachment mechanism 415 is coupled with the distal end of the delivery catheter 418. Although the delivery catheter 418 comprises a proximal end and a distal end, FIG. 4A shows only the distal end. The delivery catheter 418 comprises a conduit having two concentric lumens: a delivery channel 420 and a wire channel 422. In this at least one embodiment, the delivery channel 420 is positioned around the exterior of the wire channel 422 such that the wire channel 422 is completely encased within the delivery channel 420. Further, the delivery channel 420 and the wire channel 422 are not in communication with one another.

The delivery channel 420 of the delivery catheter 418 is used to deliver adhesive to the scaffold assembly 428. As shown in FIG. 4B, the delivery channel 420 is ring-shaped, which tends to provide relatively even movement of the adhesive through the channel, but other shapes of delivery channels may be suitable. The distal end of the delivery channel 420 is in fluid communication with the delivery channel 432 of the scaffold assembly 428. In this manner, adhesive introduced into the delivery channel 420 of the delivery catheter 418 can be advanced into the delivery channel 432 of the attachment mechanism 415 and expelled onto the target tissue through the number of openings in the ferromagnetic scaffold assembly 428. In the event a magnetic adhesive is employed, the plurality of magnetic beads 430 embedded within the scaffold assembly 428 facilitate a secure connection with the magnetic adhesive by coupling therewith.

The wire channel 422 is used to facilitate communication between the sensor 106 and the memory device 104 (not shown). The wire channel 422 houses the second connecting wire 109 of the sensory lead 102. As previously described in connection with FIG. 1A, the second connecting wire 109 of the sensory lead 102 couples with both the sensor 106 and the connection assembly 105 (not shown).

In operation, the attachment assembly 415 and the sensor 106 are delivered concurrently to the pericardial space under direct camera laser Doppler probe, radioscopic or echocardiographic guidance. After the epicardial surface of the heart 10 is accessed, and the attachment mechanism 415 and the sensor 106 are delivered to the proximate location of the targeted epicardial surface. In one embodiment, the attachment mechanism 415 is positioned in the first folded position as it is guided toward the desired location on the epicardial surface of the heart 10. When the attachment mechanism 415 and the sensor 106 are positioned proximate to the desired location, a user introduces an adhesive into the delivery channel 420 of the delivery catheter 418, which can then be advanced through the channel 420 via pressure. For example, a user may squeeze an external portion of the delivery catheter 418, thereby forcing the adhesive to advance into the delivery channel 432 and through the number of openings within the scaffold assembly 428 surrounding the sensor 106. In the event the attachment mechanism 415 is introduced into the pericardial space in the first folded position, the scaffold assembly 428 necessarily moves into the second open position as the adhesive is delivered through the openings in the ferromagnetic scaffold assembly 428.

As the adhesive flows through the number of openings in the ferromagnetic scaffold assembly 428, the sensor 106 is moved into contact with the targeted epicardial surface. In one embodiment, the sensor 106 and the surface of the heart 10 may be 45° in order to maximize the receiving and transmission ability of the sensor 106. When the sensor 106 is coupled with the heart 10, the adhesive flowing through the openings in the scaffold assembly 428 is sandwiched between the epicardial surface surrounding the sensor 106 and the scaffold assembly 428. In this manner, the scaffold assembly 428 and the sensor 106 are flatly bound to the epicardial surface of the heart 10.

This embodiment of the attachment mechanism 415 provides stability for the sensor 106 by preventing the sensor 106 from becoming dislodged from the surface of the heart 10. While this embodiment employs an adhesive, such as a biological, non-biological, or magnetic glue, to adhere the sensor 106 to the surface of the heart 10, various other mechanisms of attachment may be provided to achieve the same results.

Figure 5A:
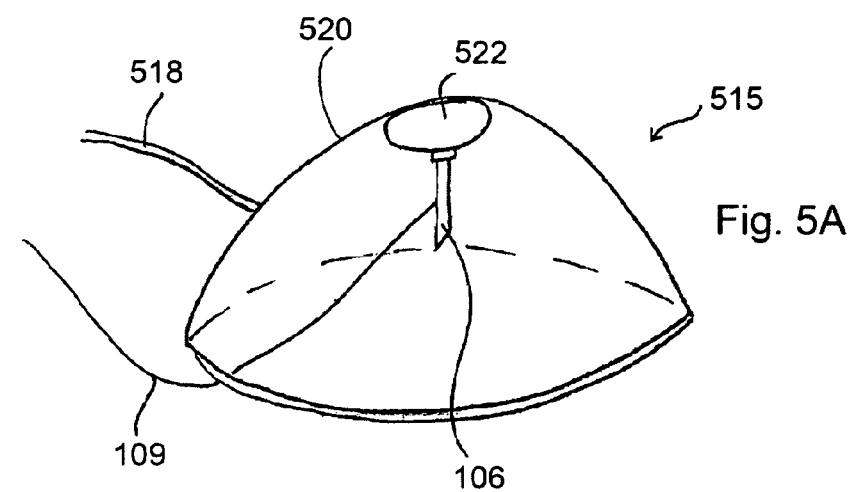
FIG. 5A shows a perspective view of at least one embodiment a sensor of an implantable monitoring system having an attachment mechanism coupled therewith.

Now referring to FIG. 5A, a perspective view of another embodiment of an attachment mechanism 515 is shown. Similar to the attachment mechanism 415, the attachment mechanism 515 may be used in conjunction with the sensory leads and sensors described herein, or with any similar sensory system for which it is beneficial to enable secure attachment to a targeted tissue.

The attachment mechanism 515 functions to secure a sensor 106 to the epicardial surface of the heart 10 using suction. In this embodiment, the attachment mechanism 515 comprises a vacuum catheter 518 coupled with a capsula 520. Further, the attachment mechanism 515 is particularly efficient if the sensor 106 comprises an arrow or anchor-like shape.

Figure 5B:
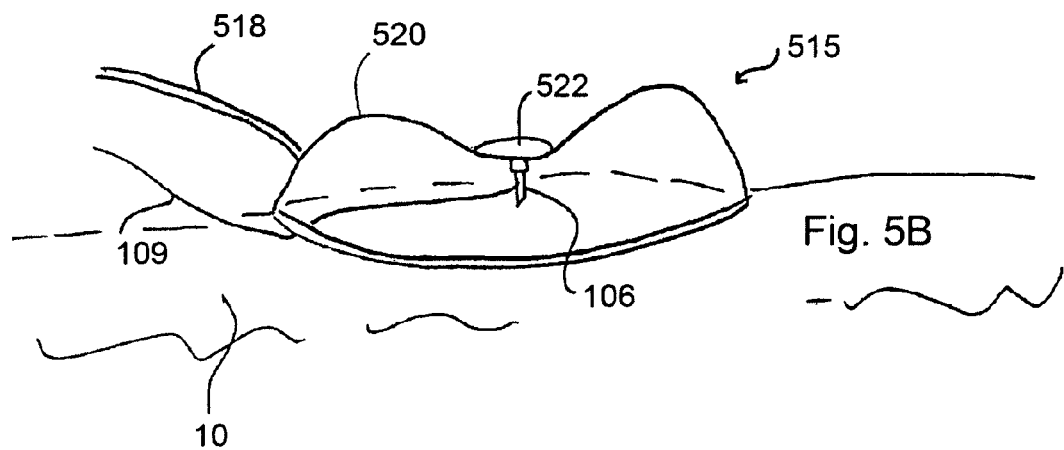
FIG. 5B shows a perspective view of the sensor of FIG. 5A wherein the attachment mechanism is partially collapsed.

In this at least one embodiment, the attachment mechanism 515 comprises a single-chambered capsula 520 coupled with a vacuum catheter 518. As shown in FIG. 5A, the capsula 520 is dish-shaped and comprises an open end a closed end, and an interior chamber; however, other shapes of capsulas may be suitable. The majority of the capsula 520 is formed of a semi-flexible or flexible material; however, a hard plastic center 522 is disposed proximate to the midpoint of the capsula 520. The sensor 106 is removably coupled with the hard plastic center 522 such that the sensor 106 protrudes into the interior chamber of the capsula 520 as shown in FIGS. 5A and 5B. Similar to the embodiments shown in FIGS. 1A and 3, the second connecting wire 109 is coupled with the sensor 106 directly such that the sensor 106 is in communication with the connection assembly 502.

Referring back to FIG. 5A, the vacuum catheter 518 of the attachment mechanism 515 comprises any tubular conduit that is capable of providing suction. Although the vacuum catheter 518 comprises a proximal end and a distal end, FIGS. 5A, 5B, and 5C only illustrate the distal end of the vacuum catheter 518. The distal end of the vacuum catheter 518 is coupled with the capsula 520 such that the vacuum catheter 518 is in communication with the interior chamber of the capsula 520. In this manner, when a vacuum source is applied to the proximal end of the vacuum catheter 518, suction is provided within the interior chamber of the capsula 520.

The vacuum catheter 518 is used to provide suction such that the capsula 520 can precisely and stably bind to a targeted tissue. In one embodiment, a syringe is attached to the proximal end of the vacuum catheter 518 to provide appropriate suction through the vacuum catheter 518, and thereby within the interior chamber of the capsula 520. In addition, other types of vacuum sources may be used, such as a controlled vacuum system providing specific suction pressures.

Figure 5C:
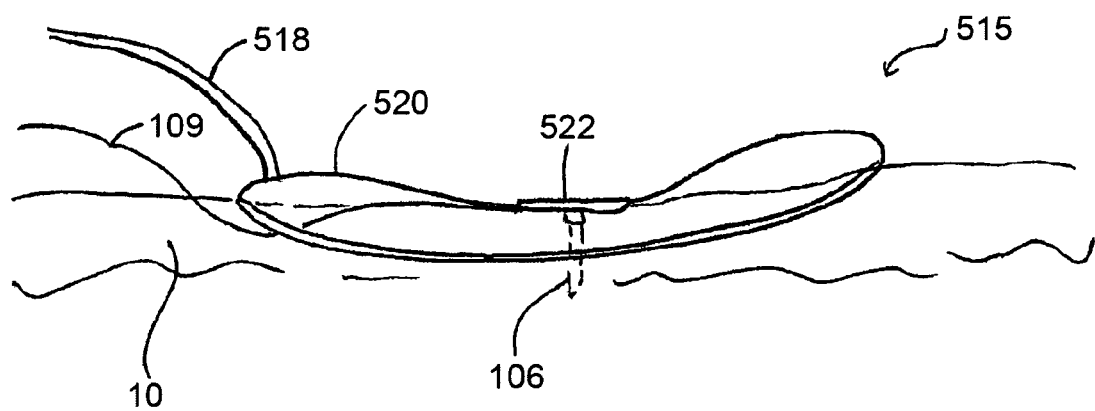
FIG. 5C shows a perspective view of the sensor of FIG. 5A wherein the attachment mechanism is fully collapsed.

Now referring to FIGS. 5B and 5C, the operation of the attachment mechanism 515 is described. When the attachment mechanism 515 and the sensor 106 are positioned proximate to the targeted epicardial surface of the heart 10, suction is provided to the interior chamber of the capsula 520 through the vacuum catheter 518. By way of the suctional force, the capsula 520 is coupled with the targeted epicardial surface on the heart 10. Accordingly, the suction forms a releasable seal between the capsula 520 and the epicardial surface.

Due to the flexible properties of the capsula 520, the force of the suction causes the capsula 520 to collapse or flatten onto the targeted epicardial surface, thereby pulling the hard plastic center 522 and the sensor 106 downward. When enough force is applied, the sensor 106 punctures the epicardial surface and is embedded within the targeted tissue. In this manner, the collapsing capsula 520 enables the insertion of the sensor 106 into the surface of the heart 10 via a pressurized introduction. Further, the clinician using the attachment mechanism 515 to deliver the sensor 106 can use the hard plastic center 522 as a guide for the placement of the sensor 106 on the heart 10. In one embodiment, an adhesive may further be applied to the sensor 106 such that the sensor 106 is retained in the heart 10 by insertion and adhesion.

After the sensor 106 is sufficiently embedded within the epicardial surface, the sensor 106 is released from the hard plastic center 522 and the capsula 520 is withdrawn. The configuration of the sensor 106 in an anchor or arrow-like shape facilitates retention of the sensor 106 within the epicardial tissue such that retraction is prevented. Accordingly, this embodiment of the attachment mechanism 515 functions to 1) locate and attach to the targeted epicardial surface; and 2) safely and accurately insert the sensor 106 into the cardiac tissue.

In at least one alternative embodiment of the attachment mechanism 515, the sensor 106 comprises a blunt shape so as not to facilitate insertion into the surface of the heart 10. In this embodiment, when the capsula 520 is collapsed and the sensor 106 is placed in contact with the surface of the heart 10, an adhesive is employed to achieve the secure placement of the sensor 106. Accordingly, an adhesive can be used in conjunction with suction to achieve the stable placement of the sensor 106.

Figure 6A:
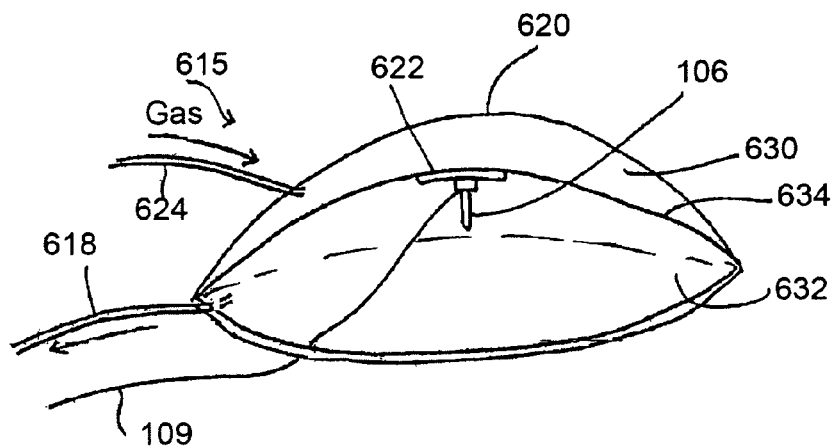
FIG. 6A shows a perspective view of at least one embodiment a sensor of an implantable monitoring system having an attachment mechanism coupled therewith.
Figure 6B:
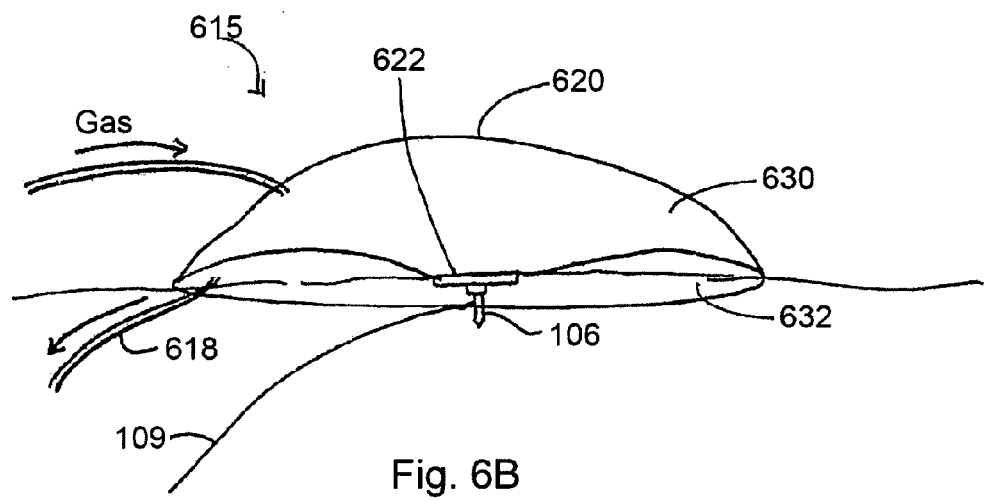
FIG. 6B shows a perspective view of the sensor of FIG. 5A wherein the flexible membrane of the attachment mechanism is fully collapsed.

Referring now to FIGS. 6A and 6B, an alternative embodiment of an attachment mechanism 615 is shown. The attachment mechanism 615 functions to secure the sensor 106 to the epicardial surface of the heart 10 using pressure and suction. Similar to the attachment mechanism 515, the attachment mechanism 615 comprises a capsula 620 having a hard plastic center 622, a sensor 106, the second connecting wire 109, and a vacuum catheter 618. This embodiment of the attachment mechanism 615 is particularly efficient if the sensor 106 comprises an arrow or anchor-like configuration. Unlike the capsula 520 of FIGS. 5A-5C, the capsula 620 of FIGS. 6A and 6B comprises two interior chambers and a delivery catheter 624. The attachment mechanism 615 can be used in conjunction with the sensory leads 102, 202 and the sensors 106, 206 described herein, or with any similar sensory system for which it is beneficial to ensure a sensory is securely attached to a targeted tissue.

In the at least one embodiment shown in FIG. 6A, the attachment mechanism 615 comprises a double-chambered capsula 620 coupled with a vacuum catheter 618 and a delivery catheter 624. Specifically, the capsula 620 in FIG. 6A is dish-shaped and comprises an open end, a closed end, and an interior. Further, the capsula 620 comprises a membrane 634 extending through the interior of the capsula 620, thereby defining an upper chamber 630 and a lower chamber 632. The upper chamber 630 is a closed chamber, enclosed by the walls of the capsula 620 and the membrane 634. Alternatively, the lower chamber 632 is open, with the membrane 634 forming the only boundary thereof.

The membrane 634 defining the upper and lower chambers 630, 632 is formed of a semi-flexible or flexible material. The hard plastic center 622 is disposed through the membrane 634 in a location proximal to the midpoint of the capsula 620. Similar to attachment mechanism 515, the sensor 106 is removably coupled with the hard plastic center 622 such that the sensor 106 protrudes into the interior of the lower chamber 632 of the capsula 620 as shown in FIG. 6A. Similar to the embodiments shown in FIGS. 1A and 3, the second connecting wire 109 is coupled with the sensor 106 and extends to the exterior of the capsula 620 through the open end of the lower chamber 632.

The vacuum catheter 618 of the attachment mechanism 615 comprises any tubular conduit that is capable of providing suction. Although the vacuum catheter 618 comprises a proximal end and a distal end, FIGS. 6A and 6B only illustrate the distal end of the vacuum catheter 618. The distal end of the vacuum catheter 618 is coupled with the capsula 620 such that the vacuum catheter 618 is in communication with the lower chamber 632 of the capsula 620. In this manner, when a vacuum source is applied to the proximal end of the vacuum catheter 618, suction is provided within the lower chamber 632 of the capsula 620.

The delivery catheter 624 of the attachment mechanism 615 comprises any tubular conduit that is capable of delivering a gas to the upper chamber 630 of the capsula 620. Although the delivery catheter 624 comprises a proximal end and a distal end, FIGS. 6A and 6B only illustrate the distal end of the delivery catheter 624. The distal end of the delivery catheter 624 is coupled with the capsula 620 such that the delivery catheter 624 is in communication with the upper chamber 630. Accordingly, the upper chamber 630 of the capsula 620 can be filled with a gas introduced through the proximal end of the delivery catheter 624. Further, due to the flexible characteristics of the membrane 634, the upper chamber 630 undergoes a downward expansion when a sufficient amount of gas is introduced therein. In this manner, as the upper chamber 630 fills with gas, the pressure within the upper chamber 630 creates a downward force on the membrane 634, thereby reducing the size of the lower chamber 632 and pushing the hard plastic center 622 and sensor 610 downward (see FIG. 6B).

In operation, the attachment mechanism 615 and the sensor 106 are positioned proximate to the targeted epicardial surface of the heart 10. Thereafter, a syringe or other means for providing suction is attached to the proximal end of the vacuum catheter 618 to provide appropriate suction therethrough. In this manner, a vacuum is created within the lower chamber 632 that is capable of suctioning the capsula 620 onto the targeted epicardial surface and forming a seal therewith.

After the capsula 620 is coupled with the epicardial surface through suction, a gas is introduced into the proximal end of the delivery catheter 624, and thereby the upper chamber 632 that is in communication therewith. In one embodiment, carbon dioxide gas may be used. The addition of gas to the upper chamber 630 increases the pressure within the upper chamber 632, thereby asserting a downward pressure on the membrane 624. The flexible nature of the membrane 624, the vacuum conditions within the lower chamber 632, and the increasing pressure in the upper chamber 630 all facilitate the expansion of the membrane 624 downward and the collapse of the lower chamber 632 (see FIG. 6B). As the lower chamber 632 collapses onto the epicardial surface, the hard plastic center 622 and the sensor 106 are pulled down into the same. In the embodiment where the sensor 106 comprises an arrow-like or anchor-like shape, the sensor 106 punctures the epicardial surface and is embedded within the targeted tissue.

After the sensor 106 is sufficiently embedded within the epicardial surface, suction through the vacuum catheter 618 and injection of gas through the delivery catheter 624 are ceased and the sensor 106 is released from the hard plastic center 622. The attachment mechanism 615 is thereafter withdrawn from the patient, leaving the sensor 106 embedded in the targeted epicardial tissue.

Figure 7:
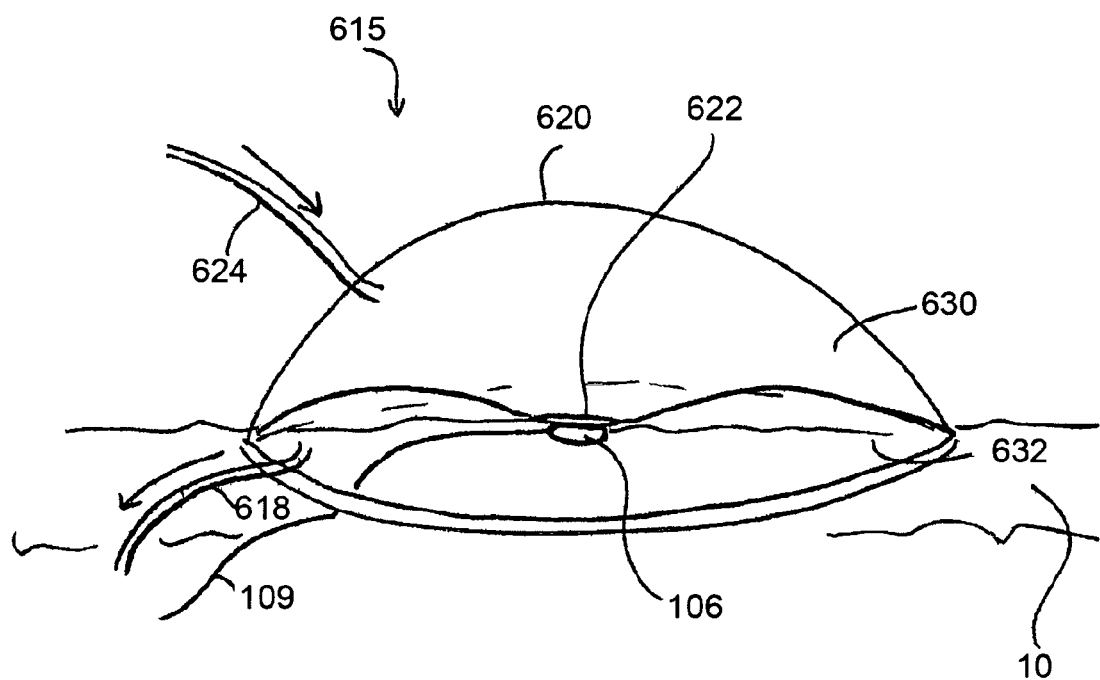
FIG. 7 shows a perspective view of at least one embodiment a sensor of an implantable monitoring system having an attachment mechanism coupled therewith.

In an alternative embodiment, the sensor 106 may be configured in an adhesive spherical design as shown in FIG. 7, for use in conjunction with the attachment mechanism 615. In this embodiment, an adhesive, including, without limitation, a biological glue, is applied to the surface of the sensor 106 such that the adhesive is employed in addition to the suction and gas injection to facilitate the secure attachment of the sensor 106 to the epicardial surface.

Figures 8A, 8B:
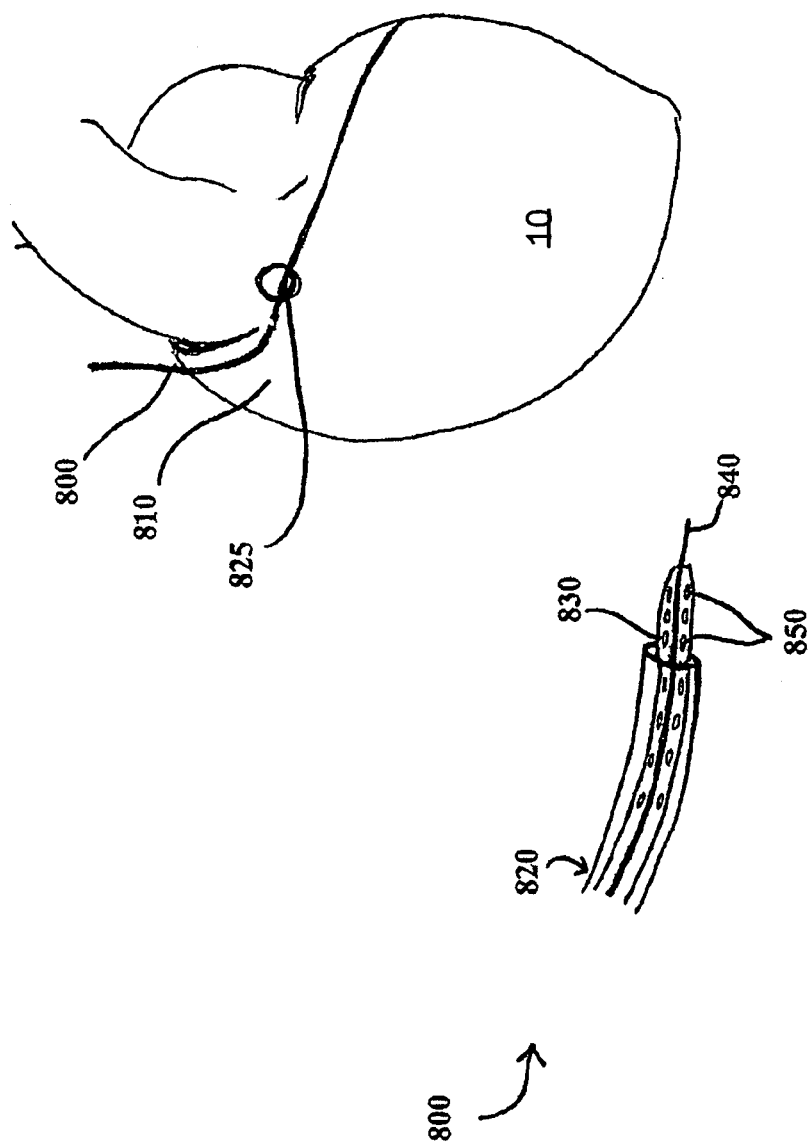
FIG. 8A shows a perspective view of at least one embodiment of an engagement catheter and a delivery catheter.
FIG. 8B shows a percutaneous intravascular pericardial delivery using at least one embodiment of an engagement catheter and another embodiment of a delivery catheter.

The various embodiments of the monitoring system 100 disclosed herein are inserted into a patient using the systems, devices and methods disclosed in the co-pending International Patent Application No. PCT/US2007/015207, the totality of which is incorporated herein by reference. FIG. 8A shows one embodiment of a catheter system 800 for providing percutaneous, intravascular access to the pericardial space through an atrial wall or the wall of the atrial appendage.

Unlike the relatively stiff pericardial sac, the atrial wall and atrial appendage are rather soft and deformable. Hence, suction of the atrial wall or atrial appendage can provide significantly more clearance of the cardiac structure from the pericardium as compared to suction of the pericardium. Furthermore, navigation from the intravascular region (inside of the heart) provides more certainty of position of vital cardiac structures than does intrathoracic access (outside of the heart). Through accessing the pericardial space, sensors may be delivered via the pericardial space and positioned in directly contact with the exterior wall of the heart without opening the chest cavity of the patient.

In the embodiment of the catheter system shown in FIG. 8A, the catheter system 800 includes an engagement catheter 820, a delivery catheter 830, and a needle 840. Although each of the engagement catheter 820, the delivery catheter 830, and the needle 840 comprise a proximal end and a distal end, FIG. 8A shows only the distal end. The engagement catheter 820 has a lumen through which the delivery catheter 830 has been inserted, and the delivery catheter 830 has a lumen through which the needle 840 has been inserted. The delivery catheter 830 also has a number of openings 850 that can be used to transmit fluid from the lumen of the catheter to the heart tissue in close proximity to the distal end of the catheter.

Figures 9A, 9B, 9C:
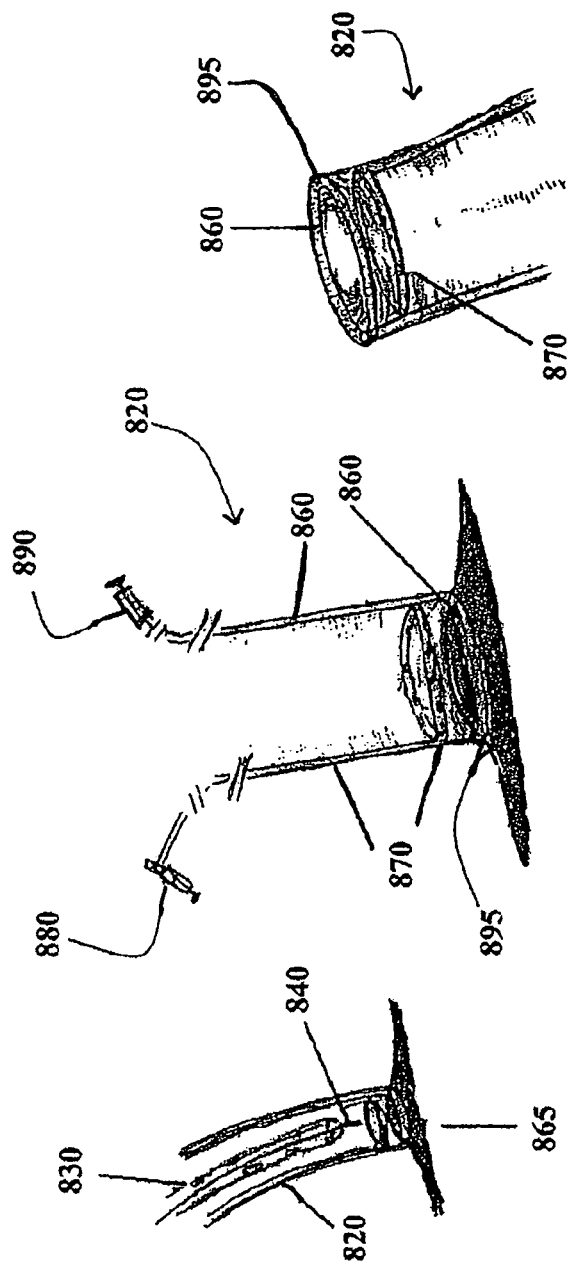
FIG. 9A shows a percutaneous intravascular technique for accessing the pericardial space through a right atrial wall or atrial appendage using the engagement and delivery catheters shown in FIG. 8A.
FIG. 9B shows the embodiment of the engagement catheter shown in FIG. 9A.
FIG. 9C shows another view of the distal end of the engagement catheter embodiment shown in FIGS. 9A and 9B.

As shown in more detail in FIGS. 9A, 9B, and 9C the engagement catheter 820 includes a vacuum channel 860 used for suction of a targeted tissue 865 in the heart and an injection channel 870 used for infusion of substances to the targeted tissue 865, including, for example and without limitation, a biological or non-biological degradable adhesive. As shown in FIGS. 9B and 9C, the injection channel 870 is ring-shaped, which tends to provide relatively even dispersal of the infused substance over the targeted tissue, but other shapes of injection channels may be suitable. A syringe 880 is attached to injection channel 870 for delivery of the appropriate substances to the injection channel 870, and a syringe 880 is attached to the vacuum channel 860 through a vacuum port (not shown) at the proximal end of the engagement catheter 820 to provide appropriate suction through vacuum channel 860. At the distal end of the engagement catheter 820, a suction port 895 is attached to the vacuum channel 860 for contacting targeted tissue 865, such that suction port 895 surrounds targeted tissue 865, which is thereby encompassed within the circumference of suction port 895. Although the syringe 890 is shown in FIG. 9B as the vacuum source providing suction for the engagement catheter 820, other types of vacuum sources may be used, such as a controlled vacuum system providing specific suction pressures. Similarly, the syringe 880 serves as the external fluid source in the embodiment shown in FIG. 9B, but other external fluid sources may be used.

A route of entry for use of various embodiments disclosed herein is through the jugular or femoral vein to the superior or inferior vena cava, respectively, to the right atrial wall or atrial appendage (percutaneously) to the pericardial sac (through puncture).

Referring now to FIG. 8B, an engagement catheter 800 is placed via standard approach the jugular or femoral vein. The catheter 800, which may be 4 or 5 Fr., is positioned under fluoroscopic or echocardiographic guidance into the right atrial appendage 810. Suction is initiated to aspirate a portion of the atrial appendage 810 away from the pericardial sac that surrounds the heart. As explained herein, aspiration of the heart tissue is evidenced when no blood can be pulled back through the engagement catheter 800 and, if suction pressure is being measured, when the suction pressure gradually increases. A small perforation is made in the aspirated atrial appendage 810 with a needle such as needle 840, as shown in FIGS. 8A and 9A. A guide wire (not shown) can then be advanced through the delivery catheter 830 into the pericardial space to secure the point of entry 825 through the atrial appendage 810 and to guide further insertion of the delivery catheter 830 or another catheter. Fluoroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg).

Although aspiration of the atrial wall or the atrial appendage retracts the wall or appendage from the pericardial sac to create additional pericardial space, carbon dioxide gas can be delivered through a catheter, such as the delivery catheter 830, into the pericardial space to create additional space between the pericardial sac and the heart surface.

FIGS. 10A, 10B, 10C, and 10D show another embodiment of an engagement catheter as disclosed herein. The engagement catheter 900 is an elongated tube having a proximal end 910 and a distal end 920, as well as two lumens 930, 940 extending between proximal end 910 and distal end 920. The lumens 930, 940 are formed by the concentric inner wall 950 and outer wall 960, as particularly shown in FIGS. 10B and 10C. At the proximal end 910, the engagement catheter 900 includes a vacuum port 970, which is attached to the lumen 930 so that a vacuum source can be attached to the vacuum port 970 to create suction in the lumen 930, thereby forming a suction channel. At the distal end 920 of the catheter 900, a suction port 980 is attached to the lumen 930 so that the suction port 980 can be placed in contact with the heart tissue 975 (see FIG. 10D) for aspirating the tissue, thereby forming a vacuum seal between the suction port 980 and the tissue 975 when the vacuum source is attached and engaged. The vacuum seal enables the suction port 980 to grip, stabilize, and retract the tissue 975. For example, attaching a suction port to an interior atrial wall using a vacuum source enables the suction port to retract the atrial wall from the pericardial sac surrounding the heart, which enlarges the pericardial space between the atrial wall and the pericardial sac.

As shown in FIG. 10C, two internal lumen supports 1010, 1020 are located within the lumen 930 and are attached to the inner wall 950 and the outer wall 960 to provide support to the walls. These lumen supports divide the lumen 930 into two suction channels. Although the internal lumen supports 1010, 1020 extend from the distal end 920 of the catheter 900 along a substantial portion of the length of the catheter 900, the internal lumen supports 910, 920 may or may not span the entire length of the catheter 900. Indeed, as shown in FIGS. 10A, 10B, and 10C, the internal lumen supports 1010, 1020 do not extend to the proximal end 910 to ensure that the suction from the external vacuum source is distributed relatively evenly around the circumference of the catheter 900. Although the embodiment shown in FIG. 10C includes two internal lumen supports, other embodiments may have just one internal support or even three or more such supports.

Figure 10D:
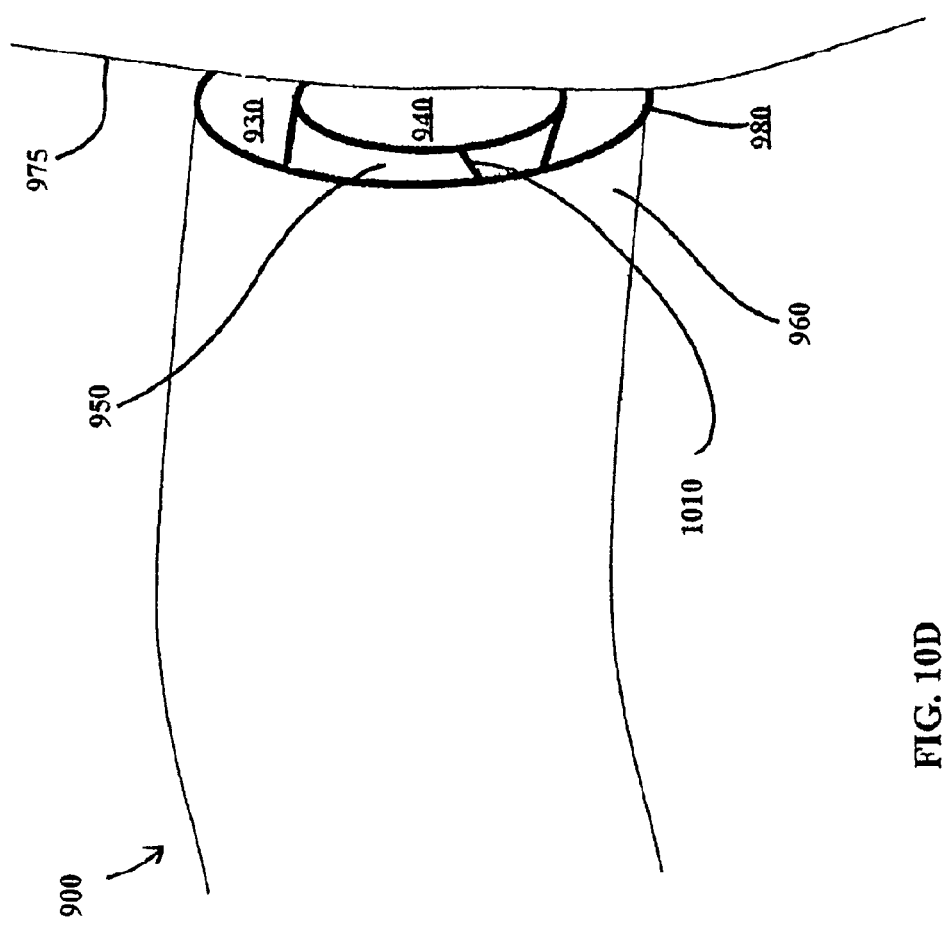
FIG. 10D shows the engagement catheter of FIG. 10A approaching a heart wall from the inside of the heart.

FIG. 10D shows the engagement catheter 900 approaching the heart tissue 975 for attachment thereto. It is important for the clinician performing the procedure to know when the suction port has engaged the tissue of the atrial wall or the atrial appendage. For example, in reference to FIG. 10D, it is clear that the suction port 980 has not fully engaged the tissue 975 such that a seal is formed. However, because the suction port 980 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as the engagement catheter 900 approaches the atrial wall tissue (such as tissue 975) and is approximately in position, the suction can be activated through the lumen 930. A certain level of suction (e.g., about 10 mmHg) can be imposed and measured with a pressure sensor/regulator. As long as the catheter 900 does not engage the wall, some blood will be aspirated into the catheter and the suction pressure will remain the same. However, when the catheter 900 engages or attaches to the wall of the heart (depicted as the tissue 975 in FIG. 10D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

Referring now to FIGS. 11A, 11B, and 11C, there is shown a delivery catheter 1050 comprising an elongated hollow tube 1080 having a proximal end 1060, a distal end 1070, and a lumen 1085 along the length of the catheter. Extending from the distal end 1070 is a hollow needle 1090 in communication with the lumen 1085. The needle 1090 is attached to the distal end 1070 in the embodiment of FIGS. 11A, 11B, and 11C, but, in other embodiments, the needle may be removably attached to, or otherwise located at, the distal end of the catheter (see FIG. 8A). In the embodiment shown in FIGS. 11A, 11B, and 11C, as in certain other embodiments having an attached needle, the junction (i.e., site of attachment) between the hollow tube 1080 and the needle 1090 forms a security notch 1110 circumferentially around the needle 1090 to prevent the needle 1090 from over-perforation. Thus, when a clinician inserts the needle 1090 through an atrial wall to gain access to the pericardial space, the clinician will not, under normal conditions, unintentionally perforate the pericardial sac with the needle 1090 because the larger diameter of the hollow tube 1080 (as compared to that of the needle 1090) at the security notch 1110 hinders further needle insertion. Although the security notch 1110 is formed by the junction of the hollow tube 1080 and the needle 1090 in the embodiment shown in FIGS. 11A, 11B, and 11C, other embodiments may have a security notch that is configured differently. For example, a security notch may include a band, ring, or similar device that is attached to the needle a suitable distance from the tip of the needle. Like the security notch 1110, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 11B, the needle 1090 may be connected to a strain gauge 1115 as part of the catheter assembly. When the needle 1090 contacts tissue (not shown), the needle 1090 will be deformed. The deformation will be transmitted to the strain gauge 1115 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as the catheter 1050 shown in FIGS. 11A, 11B, and 11C, is used with an engagement catheter, such as the catheter 900 shown in FIGS. 10A, 10B, 10C, and 10D, to gain access to the pericardial space between the heart wall and the pericardial sac. For example, the engagement catheter 900 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as the lumen 940 shown in FIGS. 10B and 10C. Use of the guide wire enables more effective navigation of the delivery catheter 1050 and prevents the needle 1090 from damaging the inner wall 950 of the engagement catheter 900. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

In one embodiment, a delivery catheter, such as the delivery catheter 1050, may be configured to deliver components of a monitoring system 100, 200 to the pericardial sac. For example, the lumen 1085 of the delivery catheter 1050 may be used for delivering the sensory lead 102 into the pericardial space after the needle 1090 is inserted through the atrial wall or the atrial appendage. In this embodiment, after the needle 1090 is inserted through the atrial wall or the atrial appendage, the delivery catheter 1050 to which the needle 1090 is attached is withdrawn from inner lumen of the engagement catheter. Thereafter, a second delivery catheter configured to deliver components of the monitoring system 100 is inserted through the inner lumen of the engagement catheter and advanced into the pericardial space. After the distal end of the second delivery catheter is positioned in the pericardial space, the at least one sensor 106 of the sensory lead 102 is delivered such that the sensor 106 is positioned adjacent to a targeted epicardial surface of the heart 10. The sensor 106 is then attached to the epicardial surface pursuant to the methods previously described herein.

After the sensors 106 are securely coupled with the epicardial surface of the heart 10, the delivery catheter 1050 is withdrawn slightly, allowing the second connecting wire 109 to extend therefrom. When the distal end of the delivery catheter 1050 is positioned within the interior of the heart proximate to the puncture in the heart wall, the connection assembly 105 is inserted into the puncture with the first end 120 positioned within the interior of the heart 10 and the second end 122 positioned within the epicardial space (see FIG. 1B). In this manner, the puncture is sealed and a conduit is provided through which the data collected from the surface of the heart 10 by the sensors 102 can be transferred to the memory device 104 positioned subcutaneously.

After the connection assembly 105 is secured, the delivery catheter 1050 is withdrawn through the inner lumen of the engagement catheter. As the delivery catheter 1050 is withdrawn, the first connecting wire 108 is allowed to remain in the inner lumen of the engagement catheter. In this manner, when the engagement catheter is withdrawn from the blood vessel, the first connecting wire 108 remains within the blood vessel (similar to the placement of pacemaker leads), thereby maintaining communication with the sensory lead 105 positioned on the heart 10 and the memory device 104. The memory device 104 may be implanted subcutaneously in any location on the body, so long as a connection is maintained with the first connecting wire 108.

When it is desirable to have the connection assembly 105 positioned adjacent to the epicardial surface of the heart 10 (as opposed to secured within an opening in the wall of the heart 10), the delivery catheter 1050 can be operated to seal the puncture in the wall of the heart 10, thereby preventing any leakage into the pericardial sac. In this embodiment, the delivery catheter 1050 further comprises a sealing system (not shown) configured to seal the puncture in the wall of the heart 10 after the sensory lead 102 is delivered to the epicardial surface thereof. In one embodiment, the sealing system may employ a biodegradable adhesive material, such as fibrin glue or cianometacrilate, to effectively seal the puncture.

The various embodiments disclosed herein may be used by clinicians, for example and among other things: (1) to perform transeptal puncture and delivery of a catheter through the left atrial appendage for electrophysiological therapy, biopsy, etc.; (2) to deliver and place epicardial, right atrial, and right and left ventricle pacing leads; and (3) to visualize the pericardial space with endo-camera, scope, or laser Doppler probe to navigate the epicardial surface of the heart for therapeutic delivery, diagnosis, lead placement, mapping, etc. Many other applications, not explicitly listed here, are also possible and within the scope of the present disclosure.

While various embodiments of devices, systems, and methods for accessing the heart tissue have been described in considerable detail herein, the embodiments are merely offered by way of non-limiting examples of the invention described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof, without departing from the scope of the invention. Indeed, this disclosure is not intended to be exhaustive or to limit the scope of the invention. The scope of the invention is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present invention.

It is therefore intended that the invention will include, and this description and the appended claims will encompass, all modifications and changes apparent to those of ordinary skill in the art based on this disclosure.

The invention claimed is:

1. A sensor assembly for collecting physiologic data from a targeted tissue, the sensory assembly comprising:
    a capsula having an exterior wall and a disk, the exterior wall comprising a flexible material and defining a closed end, an open end, and an interior space and the disk coupled with the closed end of the exterior wall;
    a vacuum catheter having a proximal end and a distal end, the distal end of the vacuum catheter coupled with the exterior wall of the capsula and in communication with the interior space of the capsula; and
    at least one sensor capable of collecting physiologic data from a targeted tissue, the at least one sensor removably coupled with the disk of the capsula such that the at least one sensor extends into the interior space of the capsula;
    wherein the open end of the capsula is configured to removably attach to a targeted tissue such that the application of suction to the vacuum catheter is capable of forming a reversible seal with the targeted tissue; and
    wherein when the at least one sensor is coupled with the targeted tissue, the at least one sensor is configured to remain coupled with the targeted tissue such that the sensor pulls away and is released from the disk.

2. The sensor assembly of claim 1, wherein the at least one sensor comprises an arrow-like or anchor-like shape.

3. The sensor assembly of claim 1, further comprising a connecting wire for transferring physiologic data collected by the at least one sensor, the connecting wire comprising a distal end coupled with the at least one sensor and a proximal end extending through the open end of the capsula.

4. The sensor assembly of claim 1, wherein the exterior wall of the capsula is capable of shifting from a first upright position to a second collapsed position when a vacuum is maintained within the interior space of the capsula.

5. The sensor assembly of claim 1, wherein the at least one sensor further comprises an adhesive applied thereon.

6. A method for attaching a sensory assembly to a surface of a targeted tissue comprising the steps of:
    providing a sensor assembly comprising:
    a capsula having an exterior wall and a disk, the exterior wall comprising a flexible material and defining a closed end, an open end, and an interior space and the disk coupled with the closed end of the exterior wall;
        a vacuum catheter having a proximal end and a distal end, the distal end of the vacuum catheter coupled with the exterior wall of the capsula and in communication with the interior space of the capsula; and
        at least one sensor capable of collecting physiologic data from a targeted tissue, the at least one sensor removably coupled with the disk of the capsula such that the at least one sensor extends into the interior space of the capsula;
        wherein the open end of the capsula is configured to removably attach to a targeted tissue such that the application of suction to the vacuum catheter is capable of forming a reversible seal with the targeted tissue, the exterior wall of the capsula is capable of shifting from a first upright position to a second collapsed position when suction is applied to the vacuum catheter, and when the at least one sensor is coupled with the targeted tissue, the at least one sensor is configured to remain coupled with the targeted tissue such that the sensor pulls away and is released from the disk;

positioning the sensor assembly proximate to a targeted tissue surface;

coupling the open end of the capsula with the targeted tissue surface by applying a suctional force to the proximal end of the vacuum catheter;

coupling the at least one sensor with the surface of the targeted tissue surface by shifting the exterior wall of the capsula to the second collapsed position;

ceasing the suctional force through the vacuum catheter;

uncoupling the at least one sensor from the disk of the capsula; and withdrawing the sensor assembly with the at least one sensor remaining coupled with the targeted tissue surface.

7. The method of claim 6, wherein the at least one sensor of the sensor assembly comprises an arrow-like or anchor-like shape.

8. The method of claim 7, wherein the step of coupling the at least one sensor with the surface of the targeted tissue surface by shifting the exterior wall of the capsula to the second collapsed position further comprises inserting the at least one sensor into the targeted tissue surface.

9. The method of claim 6, wherein the step of coupling the at least one sensor with the surface of the targeted tissue surface by shifting the exterior wall of the capsula to the second collapsed position further comprises increasing the suctional force applied to the proximal end of the vacuum catheter.

10. The method of claim 6, wherein the step of coupling the at least one sensor with the surface of the targeted tissue surface by shifting the exterior wall of the capsula to the second collapsed position further comprises the steps of:

applying an amount of adhesive to the at least one sensor; and sandwiching the amount of adhesive on the at least one sensor between the sensor and the surface of the targeted tissue.

11. The method of claim 6, wherein the step of positioning the sensor assembly proximate to a targeted tissue surface further comprises the steps of:

inserting the sensor assembly into a catheter comprising a proximal end and a distal end;

delivering the distal end of the catheter containing the sensor assembly proximate to the targeted tissue surface through catheterization and percutaneous methods;

advancing the sensor assembly through the distal end of the catheter; and withdrawing the catheter.

12. The method of claim 7, wherein the step of coupling the at least one sensor with the surface of the targeted tissue surface by shifting the exterior wall of the capsula to the second collapsed position further comprises the steps of:

applying an amount of adhesive to the at least one sensor;

inserting the at least one sensor into the targeted tissue; and sandwiching the amount of adhesive on the at least one sensor between the sensor and the targeted tissue.

13. A sensor assembly for collecting physiologic data from a targeted tissue, the sensory assembly comprising:

a capsula having an exterior wall, a disk, and a flexible membrane, the exterior wall defining a closed end, an open end, and an interior space, the disk coupled with the flexible membrane, and the flexible membrane extending through the interior space and defining an upper chamber between the flexible membrane and the closed end of the exterior wall and a lower chamber between the flexible membrane and the open end of the exterior wall;

a vacuum catheter having a proximal end and a distal end, the distal end of the vacuum catheter coupled with the exterior wall of the capsula and in communication with the upper chamber of the capsula;

at least one sensor capable of collecting physiologic data from a targeted tissue, the at least one sensor removably coupled with the disk such that the at least one sensor extends into the lower chamber of the capsula;

wherein the open end of the capsula is configured to removably attach to a targeted tissue such that the application of suction to the vacuum catheter is capable of forming a reversible seal with the targeted tissue, and the flexible membrane is capable of shifting from a first upright position to a second collapsed position when a gas is introduced into the upper chamber through the delivery catheter and suction is applied to the vacuum catheter; and wherein when the at least one sensor is coupled with the targeted tissue, the at least one sensor is configured to remain coupled with the targeted tissue such that the sensor pulls away and is released from the disk.

14. The sensor assembly of claim 13, wherein the at least one sensor comprises an arrow-like or anchor-like shape.

15. The sensor assembly of claim 13, further comprising a connecting wire for transferring physiologic data collected by the at least one sensor, the connecting wire comprising a distal end coupled with the at least one sensor, and a proximal end extending through the open end of the capsula.

16. The sensor assembly of claim 13, wherein the membrane of the capsula is capable of shifting from a first upright position to a second collapsed position when a vacuum is maintained within the lower chamber of the capsula and the pressure is increased in the upper chamber of the capsula.

17. The sensor assembly of claim 13, wherein the at least one sensor further comprises an adhesive applied thereon.

18. A method for attaching a sensory assembly to a surface of a targeted tissue comprising the steps of:

providing a sensor assembly comprising:

a capsula having an exterior wall, a disk, and a flexible membrane, the exterior wall defining a closed end, an open end, and an interior space, the disk coupled with the flexible membrane, and the flexible membrane extending through the interior space and defining an upper chamber between the flexible membrane and the closed end of the exterior wall and a lower chamber between the flexible membrane and the open end of the exterior wall, a vacuum catheter having a proximal end and a distal end, the distal end of the vacuum catheter coupled with the exterior wall of the capsula and in communication with the upper chamber of the capsula, a delivery catheter having a proximal end and distal end, the distal end of the delivery catheter coupled with the exterior wall of the capsula and in communication with the upper chamber of the capsula, at least one sensor capable of collecting physiologic data from a targeted tissue, the at least one sensor removably coupled with the disk such that the at least one sensor extends into the lower chamber of the capsula;

wherein the open end of the capsula is configured to removably attach to a targeted tissue such that the application of suction to the vacuum catheter is capable of forming a reversible seal with the targeted tissue, and the flexible membrane is capable of shifting from a first upright position to a second collapsed position when a gas is introduced into the upper chamber through the delivery catheter and suction is applied to the vacuum catheter, and wherein when the at least one sensor is coupled with the targeted tissue, the at least one sensor is configured to remain coupled with the targeted tissue such that the sensor pulls away and is released from the disk;

positioning the sensor assembly proximate to a targeted tissue surface by applying a suctional force to the proximal end of the vacuum catheter;

introducing a gas into the upper chamber of the capsula through the delivery catheter;

coupling the at least one sensor with the targeted tissue surface by shifting the flexible membrane of the capsula to the second collapsed position;

ceasing the suctional force through the vacuum catheter and the introduction of the gas through the delivery catheter;

uncoupling the at least one sensor from the disk of the capsula; and withdrawing the sensor assembly with the at least one sensor remaining coupled with the targeted tissue surface.

19. The method of claim 18, wherein the at least one sensor of the sensor assembly comprises an arrow-like or anchor-like shape.

20. The method of claim 19, wherein the step of coupling the at least one sensor with the targeted tissue surface by shifting the flexible membrane of the capsula to the second collapsed position further comprises inserting the at least one sensor into the targeted tissue surface.

21. The method of claim 18, wherein the step of coupling the at least one sensor with the targeted tissue surface by shifting the flexible membrane of the capsula to the second collapsed position further comprises increasing the suctional force applied to the proximal end of the vacuum catheter and increasing the amount of gas introduced through the delivery catheter, such that a downward force is applied to the flexible membrane.

22. The method of claim 18, wherein the step of coupling the at least one sensor with the targeted tissue surface by shifting the flexible membrane of the capsula to the second collapsed position further comprises the steps of:

applying an amount of adhesive to the at least one sensor; and allowing the adhesive to adhere to the at least one sensor and to the targeted tissue surface.

23. The method of claim 18, wherein the step of positioning the sensor assembly proximate to a targeted tissue surface further comprises the steps of:

inserting the sensor assembly into a catheter comprising a proximal end and a distal end;

delivering the distal end of the catheter containing the sensor assembly proximate to the targeted tissue surface via catheterization and percutaneous methods;

advancing the sensor assembly through the distal end of the catheter; and withdrawing the catheter.

24. The method of claim 19, wherein the step of coupling the at least one sensor with the targeted tissue surface by shifting the flexible membrane of the capsula to the second collapsed position further comprises the steps of:

applying an amount of adhesive to the at least one sensor;

inserting the at least one sensor into the targeted tissue surface; and allowing the adhesive to adhere to the at least one sensor and to the targeted tissue surface.

25. The sensor assembly of claim 1, wherein the capsula is a single-chambered capsula.

26. The sensor assembly of claim 1, wherein the capsula is dish-shaped.

27. The sensor assembly of claim 1, wherein the capsula is formed of a semi-flexible or flexible material.

28. The sensor assembly of claim 1, wherein the disk is disposed proximate to a midpoint of the capsula.

29. The sensor assembly of claim 1, wherein the suction causes the capsula to collapse or flatten onto the targeted tissue.

30. The sensor assembly of claim 29, wherein when the capsula collapses or flattens onto the targeted tissue, the at least one sensor contacts the targeted tissue.

31. The sensor assembly of claim 1, wherein the at least one sensor comprises a blunt shape so as to not facilitate insertion into the targeted tissue.

32. The sensor assembly of claim 31, wherein the at least one sensor further comprises an adhesive applied thereon, the adhesive used to secure placement of the at least one sensor to the targeted tissue.

33. The sensor assembly of claim 13, wherein the capsula is dish-shaped.

34. The sensor assembly of claim 13, wherein the disk is disposed proximate to a midpoint of the capsula.

35. The sensor assembly of claim 13, wherein the suction causes the capsula to collapse or flatten onto the targeted tissue.

36. The sensor assembly of claim 35, wherein when the capsula collapses or flattens onto the targeted tissue, the at least one sensor contacts the targeted tissue.

37. The sensor assembly of claim 13, wherein the at least one sensor comprises a blunt shape so as to not facilitate insertion into the targeted tissue.

38. The sensor assembly of claim 37, wherein the at least one sensor further comprises an adhesive applied thereon, the adhesive used to secure placement of the at least one sensor to the targeted tissue.

39. A sensor assembly for collecting physiologic data from a targeted tissue, the sensory assembly comprising:

a capsula having an exterior wall and a disk, the exterior wall comprising a flexible material and defining a closed end, an open end, and an interior space and the disk coupled with the closed end of the exterior wall;

a vacuum catheter having a proximal end and a distal end, the distal end of the vacuum catheter coupled with the exterior wall of the capsula and in communication with the interior space of the capsula; and at least one sensor capable of collecting physiologic data from a targeted tissue, the at least one sensor removably coupled with the disk of the capsula such that the at least one sensor extends into the interior space of the capsula;

wherein the open end of the capsula is configured to removably attach to a targeted tissue such that the application of suction to the vacuum catheter is capable of forming a reversible seal with the targeted tissue;

wherein when the at least one sensor is coupled with the targeted tissue, the at least one sensor is configured to remain coupled with the targeted tissue such that the sensor pulls away and is released from the disk;

wherein the at least one sensor comprises an arrow-like or anchor-like shape; and wherein the capsula is formed of a semi-flexible or flexible material.

40. The sensor assembly of claim 39, further comprising a connecting wire for transferring physiologic data collected by the at least one sensor, the connecting wire comprising a distal end coupled with the at least one sensor and a proximal end extending through the open end of the capsula.

41. The sensor assembly of claim 39, wherein the exterior wall of the capsula is capable of shifting from a first upright position to a second collapsed position when a vacuum is maintained within the interior space of the capsula.

42. The sensor assembly of claim 39, wherein the at least one sensor further comprises an adhesive applied thereon.

43. The sensor assembly of claim 39, wherein the capsula is a single-chambered capsula.

44. The sensor assembly of claim 39, wherein the capsula is dish-shaped.

45. The sensor assembly of claim 39, wherein the disk is disposed proximate to a midpoint of the capsula.

46. The sensor assembly of claim 39, wherein the suction causes the capsula to collapse or flatten onto the targeted tissue.

47. The sensor assembly of claim 46, wherein when the capsula collapses or flattens onto the targeted tissue, the at least one sensor contacts the targeted tissue.

48. A sensor assembly for collecting physiologic data from a targeted tissue, the sensory assembly comprising:
  a capsula having an exterior wall and a disk, the exterior wall comprising a flexible material and defining a closed end, an open end, and an interior space and the disk coupled with the closed end of the exterior wall;
  a vacuum catheter having a proximal end and a distal end, the distal end of the vacuum catheter coupled with the exterior wall of the capsula and in communication with the interior space of the capsula; and
  at least one sensor capable of collecting physiologic data from a targeted tissue, the at least one sensor removably coupled with the disk of the capsula such that the at least one sensor extends into the interior space of the capsula;
  wherein the open end of the capsula is configured to removably attach to a targeted tissue such that the application of suction to the vacuum catheter is capable of forming a reversible seal with the targeted tissue;
  wherein when the at least one sensor is coupled with the targeted tissue, the at least one sensor is configured to remain coupled with the targeted tissue such that the sensor pulls away and is released from the disk;
  wherein the at least one sensor comprises a blunt shape;
  wherein the at least one sensor further comprises an adhesive applied thereon, the adhesive used to secure placement of the at least one sensor to the targeted tissue; and
  wherein the capsula is formed of a semi-flexible or flexible material.

49. The sensor assembly of claim 48, further comprising a connecting wire for transferring physiologic data collected by the at least one sensor, the connecting wire comprising a distal end coupled with the at least one sensor, and a proximal end extending through the open end of the capsula.

50. The sensor assembly of claim 48, wherein the membrane of the capsula is capable of shifting from a first upright position to a second collapsed position when a vacuum is maintained within the lower chamber of the capsula and the pressure is increased in the upper chamber of the capsula.

51. The sensor assembly of claim 48, wherein the capsula is dish-shaped.

52. The sensor assembly of claim 48, wherein the disk is disposed proximate to a midpoint of the capsula.

53. The sensor assembly of claim 48, wherein the suction causes the capsula to collapse or flatten onto the targeted tissue.

54. The sensor assembly of claim 53, wherein when the capsula collapses or flattens onto the targeted tissue, the at least one sensor contacts the targeted tissue.

55. A sensor assembly for collecting physiologic data from a targeted tissue, the sensory assembly comprising:
  a capsula having an exterior wall, a disk, and a flexible membrane, the exterior wall defining a closed end, an open end, and an interior space, the disk coupled with the flexible membrane, and the flexible membrane extending through the interior space and defining an upper chamber between the flexible membrane and the closed end of the exterior wall and a lower chamber between the flexible membrane and the open end of the exterior wall;
  a vacuum catheter having a proximal end and a distal end, the distal end of the vacuum catheter coupled with the exterior wall of the capsula and in communication with the upper chamber of the capsula;
  at least one sensor capable of collecting physiologic data from a targeted tissue, the at least one sensor removably coupled with the disk such that the at least one sensor extends into the lower chamber of the capsula;
  wherein the open end of the capsula is configured to removably attach to a targeted tissue such that the application of suction to the vacuum catheter is capable of forming a reversible seal with the targeted tissue, and the flexible membrane is capable of shifting from a first upright position to a second collapsed position when a gas is introduced into the upper chamber through the delivery catheter and suction is applied to the vacuum catheter; and
  wherein when the at least one sensor is coupled with the targeted tissue, the at least one sensor is configured to remain coupled with the targeted tissue such that the sensor pulls away and is released from the disk;
  wherein the at least one sensor comprises a blunt shape; and
  wherein the at least one sensor further comprises an adhesive applied thereon, the adhesive used to secure placement of the at least one sensor to the targeted tissue.

56. The sensor assembly of claim 55, wherein the disk is disposed proximate to a midpoint of the capsula.

57. The sensor assembly of claim 55, wherein the suction causes the capsula to collapse or flatten onto the targeted tissue.

58. The sensor assembly of claim 57, wherein when the capsula collapses or flattens onto the targeted tissue, the at least one sensor contacts the targeted tissue.

* * * * *